(12) United States Patent
Masotti et al.

(10) Patent No.: US 10,945,789 B2
(45) Date of Patent: Mar. 16, 2021

(54) LASER TREATMENT OF BENIGN PROSTATIC HYPERTROPHY

(71) Applicant: ELESTA S.P.A., Calenzano (IT)

(72) Inventors: Leonardo Masotti, Sesto Fiorentino (IT); Luca Breschi, Vaiano (IT); Claudio Maurizio Pacella, Rome (IT); Gianluigi Patelli, Bergamo (IT)

(73) Assignee: ELESTA S.P.A., Calenzano (IT)

( * ) Notice: Subject to any disclaimer, the term of this patent is extended or adjusted under 35 U.S.C. 154(b) by 547 days.

(21) Appl. No.: 15/947,292

(22) Filed: Apr. 6, 2018

(65) Prior Publication Data

US 2019/0307508 A1    Oct. 10, 2019

(51) Int. Cl.
*A61B 18/20* (2006.01)
*A61B 18/18* (2006.01)
*A61B 18/14* (2006.01)
*A61B 18/00* (2006.01)

(52) U.S. Cl.
CPC .......... *A61B 18/20* (2013.01); *A61B 18/1492* (2013.01); *A61B 18/1815* (2013.01); *A61B 2018/00547* (2013.01); *A61B 2018/00577* (2013.01); *A61B 2018/00791* (2013.01)

(58) Field of Classification Search
CPC . A61B 18/20; A61B 18/1815; A61B 18/1492; A61B 2018/00577; A61B 2018/00547; A61B 2018/00791; A61B 2017/22061; A61B 2090/3784; A61B 2018/00702; A61B 2218/002; A61B 2218/007; A61B 2018/2005
See application file for complete search history.

(56) References Cited

U.S. PATENT DOCUMENTS

| 549,751 | A | * | 11/1895 | Stantial et al. | A62C 37/12 169/39 |
| 5,437,660 | A | * | 8/1995 | Johnson | A61B 18/24 606/15 |
| 2018/0042625 | A1 | | 2/2018 | McLeish | |
| 2018/0193080 | A1 | * | 7/2018 | Hoey | A61B 18/10 |

OTHER PUBLICATIONS

Zarrabi et al.: The evolution of lasers in urology. Therapeutic Advances in Urology (2011) 3(2) 81-89. http://tau.sagepub.com.
Verdaasdonk et al.: Explosive onset of continuous wave laser tissue ablation. Phys. Med. Biol., 1990, vol. 35, No. 8, 1129-1144.

(Continued)

*Primary Examiner* — Mark Bockelman
(74) *Attorney, Agent, or Firm* — McGlew and Tuttle, P.C.

(57) ABSTRACT

The method of treating benign prostatic hyperplasia comprises trans-perineally introducing at least one energy delivery device through a perineal area of the patient in a first position in a prostate of the patient. Once the energy delivery device has been introduced, energy is delivered through the delivery device to a volume of tissue of the prostate, until the volume is vaporized or sublimated and a cavity is formed in the prostate tissue. The energy delivery device can then be removed from the prostate. Vaporization of adenomatous tissue provides immediate relieve of the urethra compression.

21 Claims, 17 Drawing Sheets

(56) References Cited

OTHER PUBLICATIONS

Transperineal Laser Ablation for Percutaneous Treatment of Benign Prostatic Hyperplasia—A Prospective Study. Original Research.
Rassweiler et al.: Complications of Transurethral Resection of the Prostate (TURP)—Incidence, Management, and Prevention. European Urology 50 (2006) 969-980.
Patelli et al.: Transperineal Laser Ablation for Percutaneous Treatment of Benign Prostatic Hyperplasia—A Feasibility Study. Springer Science+Business Media New York and the Cardiovascular and Interventional Radiological Society of Europe(CIRSE) 2017.
Muschter et al.: Technique and results of interstitial laser coagulation. World Journal of Urology (1995) 13: 109-114.
McNicholas et al.: Interstitial Laser Coagulation of the Prostate—An Experimental Study. British Journal of Urology (1993), 71, 439-444.
ISSA: The Evolution of Laser Therapy in the Treatment of Benign Prostatic Hyperplasia. Reviews in Urology, vol. 7, Suppl. 9, 2005.
Henkel et al: Transurethral and Transperineal Interstitial Laser Therapy of BPH. Dept. of Urology, Klinikum Mannheim of the Univ. of Heidelberg, D-68135 Mannheim Germany, pp. 416-421.
Dr. Cowles III, et al.: A Prospective Randomized Comparison of Transurethral Resection to Visual Laser Ablation of the Prostate for the Treatment of Benign Prostatic Hyperplasia. Urology 46 (2), pp. 155-160, 1995.

\* cited by examiner

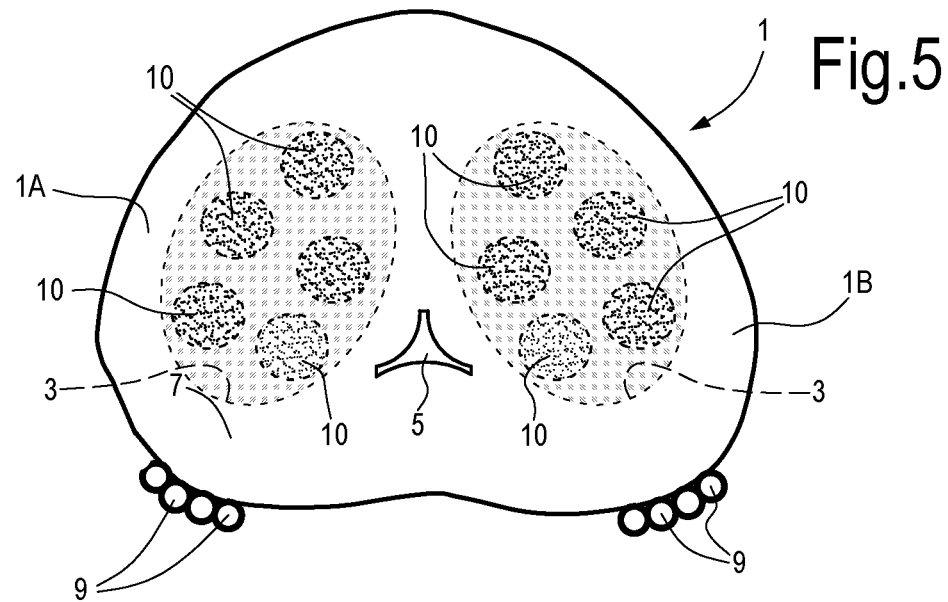
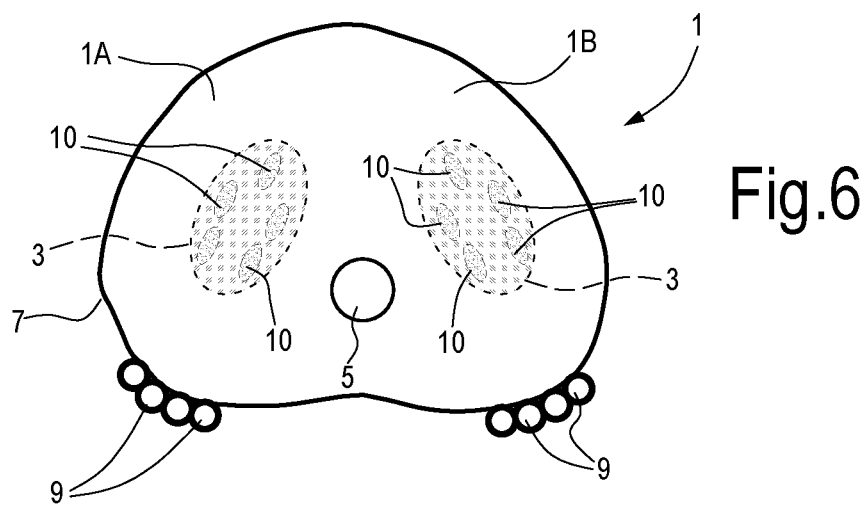

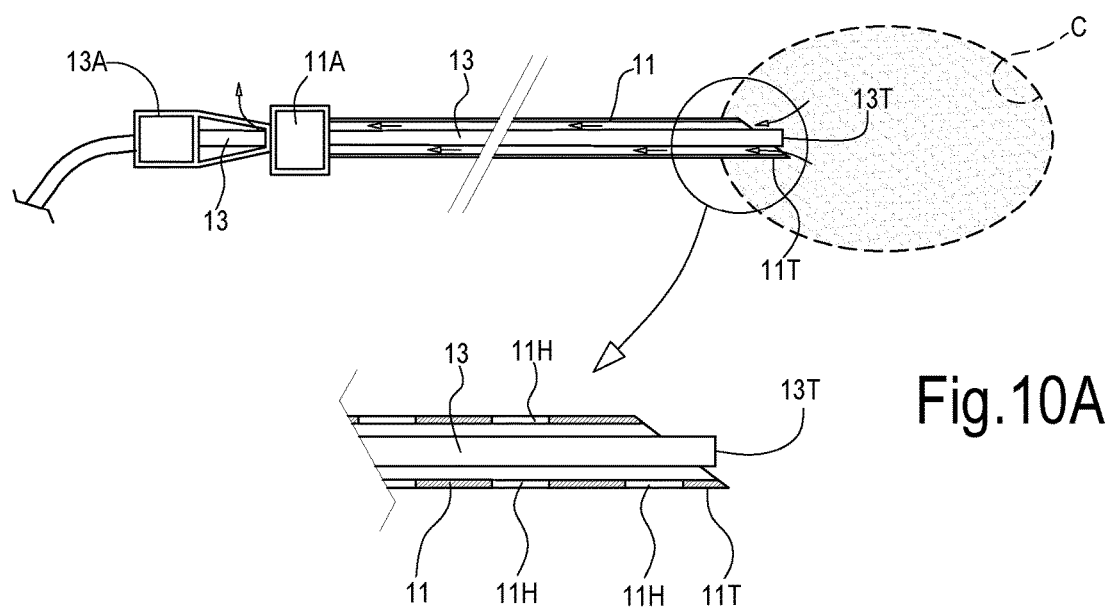
Fig.10
Fig.10A
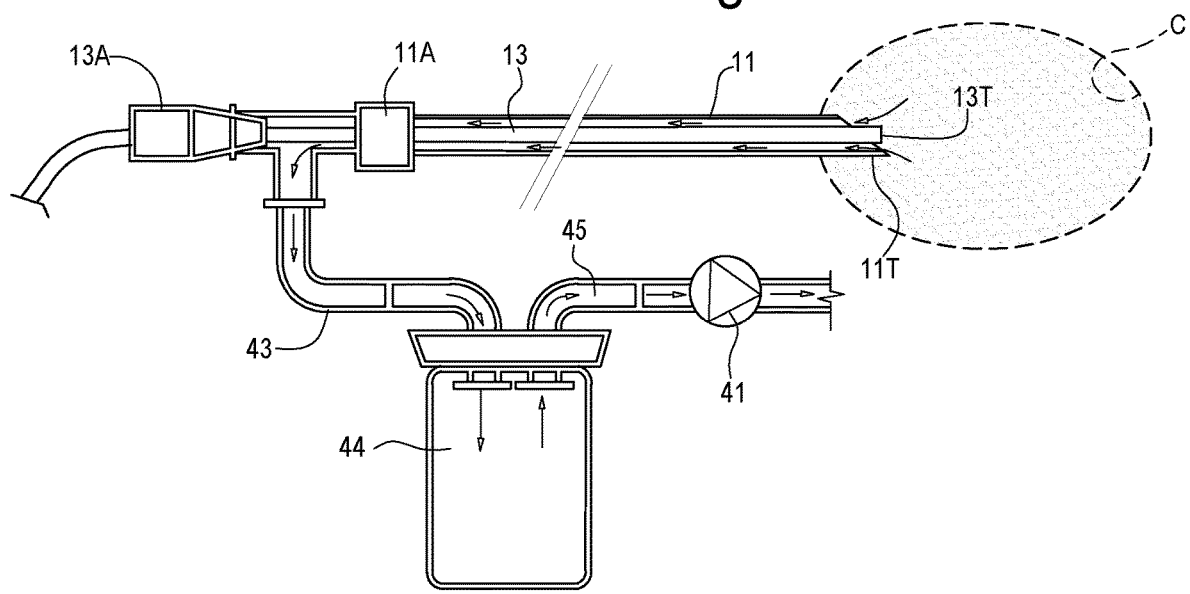
Fig.11

LASER TREATMENT OF BENIGN PROSTATIC HYPERTROPHY

TECHNICAL FIELD

Disclosed herein are ablative treatments of human or animal body. Embodiments disclosed herein specifically concern the treatment of Benign Prostatic Hyperplasia or Benign Prostatic Hypertrophy (shortly here on referred to also as BPH) by ablation therapy. Some embodiments specifically refer to laser ablation therapy.

CLINICAL BACKGROUND

Benign Prostatic Hyperplasia (BPH), also known as Benign Prostatic Hypertrophy, is a benign pathology of the prostate characterized by proliferation of prostate cellular elements. Cellular accumulation and gland enlargement may result from both epithelial and stromal proliferation and/or reduced cell death (apoptosis). The enlarged gland has been proposed to contribute to the overall lower urinary tract symptoms (LUTS).

BPH/LUTS prevalence rates ranges from 50% to 75% among men 50 years of age and older to 80% among men 70 years of age and older. The overall incidence rates ranges from 8.5 to 41 cases/1000 person per years.

The presence of moderate-to-severe LUTS was also associated with the development of acute urinary retention (AUR) as a symptom of BPH progression, increasing from a prevalence of 6.8 episodes per 1000 patient years of follow-up in the overall population to a high of 34.7 episodes in men aged 70 and older with moderate to severe LUTS.

Enlargement of the prostate involves a series of compression symptoms that also affect the dynamics of urination and greatly alter the quality of life of the affected patient. Although LUTS secondary to BPH (LUTS/BPH) is not often a life-threatening condition, the impact of LUTS/BPH on quality of life (QoL) can be significant and should not be underestimated. Some symptoms include: hesitation, weak and/or intermittent urinary stream, urinary retention, burning sensation and/or pain during urination, dysuria, urgency incontinence (urgent need to urinate), urination frequency, urine leakage, incontinence, dribbling at the end of urination, nocturia, incomplete emptying of the bladder, straining.

TURP (transurethral resection of prostate) is today the most common technique in the treatment of BPH. This technique represents an evolution of open surgery achieving improvement in LUTS symptoms with lower hospitalization time. The technique, which nowadays represents the gold standard, consists in the removal of the enlarged tissue by means of a surgical instrument called a resectoscope inserted into the penis through the urethra, such that no external incision is required, as instead in the case of open surgery. In this way, the hypertrophic tissues of the prostatic gland, which creates compression on the urethra, is sliced in small pieces and removed by the resectoscope. TURP is performed in general anesthesia or spinal anesthesia and requires from one to two hospital recovery after the procedure. A catheter is needed due to swelling that blocks urine flow in post treatment (generally left in place for at least 24 to 48 hours).

TURP is still considered an aggressive surgery involving several acute and chronic complications that can greatly affect the life of the patient in post-surgery. Bleeding especially in patients receiving an anticoagulant therapy (heparin, coumadin related compounds, antiplatelet agents) remains a concern and may require, although rarely, blood transfusion.

Additional several post-treatment urinary symptoms exist, due to the fact that the urethra epithelium has been completely removed. For instance urination may be painful; a sense of urgency or frequent urination 6 to 8 weeks after TURP has also been reported by patients. One of the possible permanent side effects of TURP is retrograde ejaculation which results when the tiny sphincter muscle that usually blocks off the bladder during ejaculation is damaged during the procedure. This side effect can force patient to sterility. The main complications of TURP and their incidence are:

- temporary difficulty urinating (urinary retention): 3%
- urinary tract infection: 1.7%
- erectile dysfunction: 2.1-11%
- heavy bleeding: transfusion rate 0.4%
- difficulty holding urine (early urge incontinence): 30-40%
- need for retreatment due to urethral strictures (2.2-9.8%)
- bladder neck contractures (0.3-9.2%)

In order to improve the patient's quality of life, a number of mini-invasive techniques have been developed to achieve symptomatic remission with reduced hospitalization time and less complication rates. Based on the different approaches on which they are based, these techniques can be grouped as follows:

A. Techniques aimed at immediately removing an excess hypertrophic tissue (as TURP but with less complications and side effects). In this sense, PVP (Photo Selective Vaporization, HoLAP Holmium Laser Ablation, HoLRP holmium laser resection, HoLEP-TuLEP Holmium Laser Enucleation, Thulium Laser Enucleation) have been developed. All of these techniques are performed by a trans-urethral approach using a cystoscope and include the use of power laser that is brought into the working area by contact or non-contact optical fibers to vaporize or resect hypertrophic tissue. Among techniques of this first group, the following can be mentioned:

a. Visual Laser Ablation of the Prostate (VLAP): This procedure is performed by trans-urethral approach and consists of lasing prostatic tissue in a noncontact fashion to create an area of heat-induced coagulative necrosis that extends about 10 mm into the tissue. Edema and prolonged sloughing of the coagulated tissue leads to irritation at the level of the lower urinary tract and to urinary retention requiring long periods of catheterization, up to 3 months, in up to 30% of cases;

b. Photo Selective Vaporization (PVP): According to this technique, the urethral and periurethral tissue that causes obstruction is vaporized with the purpose of reopening the urinary duct immediately. A KTP laser (wavelength of 532 nm, visible green light) with a side firing fiber in a non-contact mode is used for this application. This wavelength is strongly absorbed by hemoglobin and therefore has a very short absorption depth in well-vascularized tissue such as the prostate;

c. Holmium Laser Ablation (HoLAP): An Holmium laser is used to produce vaporization of the tissue;

d. Holmium Laser Resection of Prostate (HoLRP): This technique expects to use high-density laser energy to vaporize/incising exceeding tissue which is cut into small pieces that fall into the bladder and are then subsequently expelled;

e. Holmium-Thulium Laser Enucleation (HoLEP-TuLEP): Resection of the entire hypertrophic lobe is achieved through a contact optical fiber that vaporizes and separates tissues. The large removed lobes fall into the bladder and are removed by morcellation, which takes considerable time especially for big prostates;

f. Trans-Urethral Incision of the Prostate (TUIP): a contact optical fiber and a high energy laser are used to produce an incision in the periurethral tissue that behaves as an alternative urine channel, B. Techniques aimed at preserving the prostatic urethra and its urothelium. These techniques usually exploit a minimally invasive approach and consist of placing an energy applicator directly into the prostatic adenoma by a cystoscope. Radiofrequency, microwave, or laser energy are released into the adenoma and, due to tissue absorption mechanisms, are transformed into heat with increasing local temperature. Temperature and exposure time induce irreversible cell damage and coagulation of small vessels with subsequent cell death in the surrounding tissue. Necrotic tissue is subsequently reabsorbed by the physiological wound healing mechanism of the human body and a prostatic volume reduction takes place, with consequent remission of BPH symptoms. There is also the possibility of obtaining necrosis of the tissues by the use of cryoablation, applied to the hypertrophic area resulting from several freezing-unfreezing cycles. Thermal energy techniques are reported below:

a) The radiofrequency technique has been named Transurethral Needle Ablation (TUNA). It involves positioning electric needles through the urethra in the hypertrophic part and generating alternating electric current between the needle tips and a recovery plate placed on the patient's skin (usually behind the legs). The current heats the prostatic tissue by Joule effect and determines cell death due to increased temperature. Urethra burns and consequent damages may occur due to incorrect needle positioning and to poor flow control of the current circulating in low impedance paths. These effects are unpredictable and thus unavoidable;

b) The procedure using microwaves on the prostate is called Transurethral Microwave Therapy (TUMT) and consists of a catheter with an antenna that is placed in the urethra through a blistered bladder balloon. The portion of the urethral tissue facing the antenna undergoes the highest temperatures of the generated thermal field and this usually causes irreversible necrosis of the urethral and surrounding tissues;

c) The technique using laser radiation to obtain tissue coagulation goes under the name of Interstitial Laser Coagulation (ILC). The procedure is performed by placing laser-diffusing fibers directly into the prostatic adenoma, either via the transurethral cystoscopic approach, or the perineal approach. The ILC laser technique uses particular optical diffusers to avoid overheating the tissues close to the tip of the flat type fiber optic. These fiber tip diffusers allow treating extended tissue portions by maintaining optical density at levels such as to induce tissue coagulation, with temperatures below 100° C. Some systems have a temperature feedback control to maintain the temperature within the desired range of 80–100° C. (Indigo® Optima Laser Treatment System; Ethicon Endo-Surgery, Cincinnati, Ohio). Optical diffusers generally have a higher caliper than bare optical fibers, because they are equipped with a protective optically transparent dome. The procedure induces substantial tissue edema and hence necessitates prolonged (7-21 days) postoperative catheterization. Retreatment rates are problematic: as high as 20% at 2 years, 41% at 3 years and 50% at 54 months.

Summarizing, trans-urethral laser techniques involving vaporization or vapor-enucleation of the exceeding tissue causes destruction of the urethral portion and it takes several weeks for new epithelization and wound healing. This type of approach implies much of the side effects and complications of treatment such as prolonged bleeding, difficulty urinating, burning, infections.

Techniques that produce tissue coagulation by a transurethral (with a cystoscope) or trans-perineal (under the ultrasound transcriptional guide) approach are aimed at preserving the functional anatomical structures of the gland and induce a coagulative necrosis in the central part of the adenoma. Anyway, the transurethral approach maintains a relative high risk of urethra damage and transperineal approach is preferred as safer and prone to less complications. However, the main drawback remains the slow improvement of symptoms which takes several weeks or months to take place.

A need therefore exists, for more efficient, less invasive treatments of BPH, which also may result in faster recovery and less post-operative discomfort for the patient.

SUMMARY

Disclosed herein is a method for treating benign prostatic hypertrophy by tissue removal, which exploits the advantages of the trans-perineal approach and energy-tissue interaction in order to remove enlarged tissues of the adenoma leaving intact all the critical prostatic and peri-prostatic structures, such as gland capsule, urethra, neurovascular bundles. Enlarged tissue removal by local energy application leads to the formation of cavities with an immediate reduction of gland compression on adjacent structures and urethra followed by the remission of LUTS symptoms.

According to one aspect, the subject matter disclosed herein concerns a method of treating benign prostatic hyperplasia in a patient in need of said treatment, comprising the following steps:

trans-perineally introducing at least one energy delivery device through a perineal area of the patient in a first position in a prostate of the patient;

delivering energy from an energy source through the energy delivery device to a first volume of tissue of said prostate, until said first volume is vaporized or sublimated and a cavity is formed in the prostate tissue;

removing the energy delivery device from the prostate; and reducing the volume of the cavity such that compression of the urethra by prostate tissue surrounding the urethra is relieved.

While several embodiments disclosed here on use laser energy, the option of using other sources of energy is not excluded. Laser beam can be easily conveyed through optical fibers, which may be beneficial since less invasive treatments are possible.

Optical fibers with very a small diameter can be introduced in the adenomatous tissue with very fine needles or introducers in order to deliver laser energy. The number of treatment sites (i.e. cavity formation by removal of hypertrophic tissue) can be arbitrary chosen. One, two or more needles and relevant fibers can be introduced in several positions of the prostate, to perform simultaneous treatment in different volumes of the prostate. In some embodiments, needles can be arranged symmetrically with respect to a sagittal plane.

In some embodiments, one optical fiber is introduced through each needle or introducer. Each optical fiber can be coupled to a respective energy source, in particular a respective laser source. Thus, in some embodiments, a number of laser sources equal to the number of needles and optical fibers simultaneously introduced in the prostate for multiple simultaneous treatments can be used. This renders the treatment faster and reduces patient's discomfort.

The energy delivered in the prostatic tissue is modulated to provoke vaporization of water contained in the tissues. The energy can also interact with carbon or other substances contained in the tissues and provoke sublimation thereof. Measures can be taken to remove gaseous material resulting from the energy/tissue interaction. As understood herein, gaseous material can include gases or vapors resulting from vaporization or sublimation of tissue.

The vaporization and possible sublimation generate cavities in the tissue, which can result in immediate reduction of the bulk of the gland, and therefore immediate relieve of the compression provoked by swollen adenomatous tissue on the urethra. The more the tissue removal, the more effective the treatment is. Single cavities generated by several energy applicators, such as optical fibers, can also merge in a larger cavity, depending on the distance between the tips of the optical fibers used during treatment and treatment parameters.

The trans-perineal approach is less traumatic than trans-urethral or trans-rectum approach and allows a lower risk of infections and is performed under local anesthesia, or even without anesthesia, if thin needles are used. As a consequence, the described treatment can be carried out in out-patient setup without general or spinal anesthesia with very short recovery times for the patient and less or no hospitalization costs. Moreover, as critical prostate structures are preserved, in particular the urethral lumen, catheterization can be reduced or avoided.

Presently preferred embodiments involve the use of optical fibers which are introduced through thin needles that are inserted into the gland under image monitoring (ultrasound or magnetic resonance imaging). Optical fibers may have a core diameter preferably ranging from 100 to 500 micrometers. Thin optical fibers can be introduced through very thin needles, e.g. 25 G-20 G caliper needles, which can be used without local anesthesia.

According to a further aspect, disclosed herein is a method of removing tissue form an organ of a patient, comprising the following steps:

introducing at least one energy delivery device in a first position in an organ of the patient;

delivering energy from an energy source through the energy delivery device to a first volume of tissue of said organ, until said first volume is vaporized or sublimated and a cavity is formed in the organ tissue;

removing the energy delivery device from the organ.

Several further features and embodiments of the methods disclosed herein are described in more detail here on and are set forth in the appended claims.

BRIEF DESCRIPTION OF THE DRAWINGS

A more complete appreciation of the disclosed embodiments of the invention and many of the attendant advantages thereof will be readily obtained as the same becomes better understood by reference to the following detailed description when considered in connection with the accompanying drawings, wherein:

FIG. 5 illustrates a cross-sectional view similar to FIGS. 1 and 2, in a further embodiment, during or prior to the treatment;

FIG. 6 illustrates the same view of FIG. 5 after treatment;

FIG. 10 illustrates a schematic cross-sectional view in a sagittal plane of a needle and optical fiber arrangement with improved gas removing facilities, aimed at removing gaseous products resulting from the tissue/laser interaction and resulting tissue vaporization and sublimation;

FIG. 10A illustrates an enlargement of a detail of FIG. 10;

FIGS. 11 and 12 illustrate schematic cross-sectional views similar to FIG. 10 of further embodiments with improved gas removing facilities;

DETAILED DESCRIPTION OF EMBODIMENTS

The following detailed description of exemplary embodiments refers to the accompanying drawings. The same reference numbers in different drawings identify the same or similar elements. Additionally, the drawings are not necessarily drawn to scale. Also, the following detailed description does not limit the invention. Instead, the scope of the invention is defined by the appended claims.

Reference throughout the specification to "one embodiment" or "an embodiment" or "some embodiments" means that the particular feature, structure or characteristic described in connection with an embodiment is included in at least one embodiment of the subject matter disclosed. Thus, the appearance of the phrase "in one embodiment" or "in an embodiment" or "in some embodiments" in various places throughout the specification is not necessarily referring to the same embodiment(s). Further, the particular features, structures or characteristics may be combined in any suitable manner in one or more embodiments.

In embodiments disclosed herein, BPH is treated with a mini-invasive procedure using energy applicators introduced into the prostate through the trans-perineal route. Embodiments disclosed herein use laser energy conveyed in situ by means of optical fibers. The laser radiation parameters are selected such that water contained in the tissue is vaporized and other substances contained in the prostatic tissue can sublimate. The resulting gaseous by-products of the tissue/laser interaction can be removed, possibly with the aid of ad-hoc removing devices. Contrary to treatments of the current art, which are mainly based on tissue denaturation and subsequent tissue resorption through biological action by the patient's body, an immediate reduction in volume of the gland is achieved, which results in immediate relieve of the BPH symptoms, mainly linked to compression of the urethral lumen.

Figure 1:
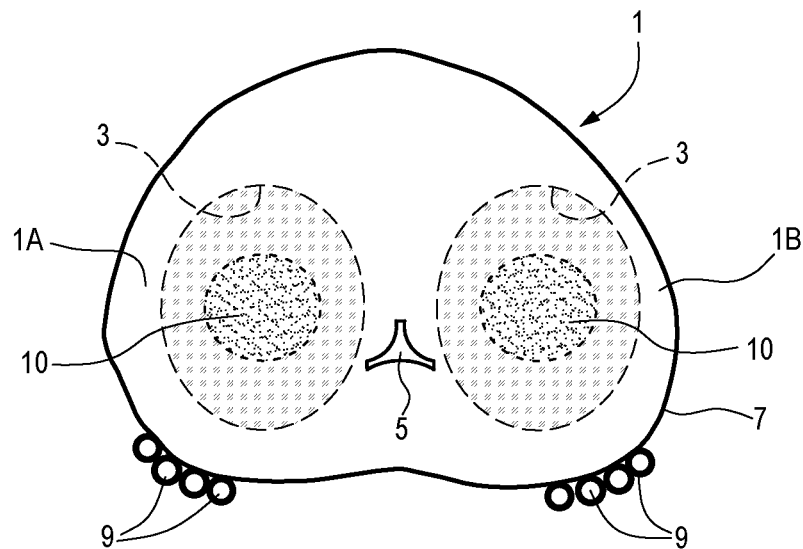
FIG. 1 illustrates a schematic cross-sectional view of a prostate affected by BPH.
Figure 2:
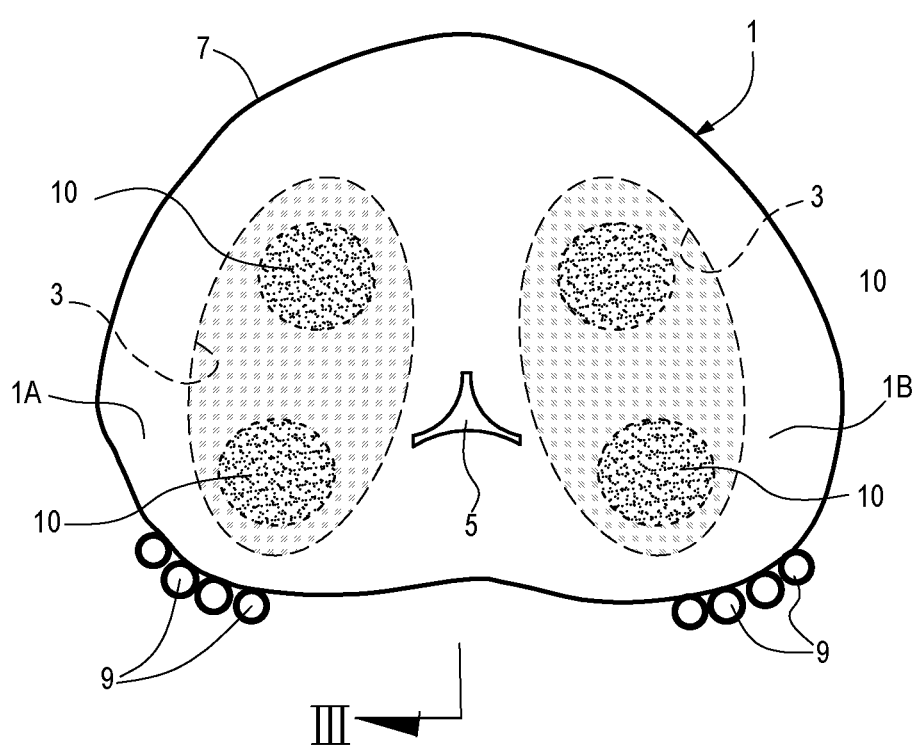
FIG. 2 illustrates another schematic cross-sectional view, according to a sagittal plane, of a prostate affected by BPH.

Turning now to the figures, FIGS. 1 and 2 illustrate two schematic sectional views along a transverse plane, i.e. orthogonal to the sagittal plane, of exemplary prostatic glands 1 affected by BPH. The two glands 1 differ from one another as far as their total dimension is concerned. The prostate of FIG. 1 is larger than the one of FIG. 2. Both prostatic glands 1 contain adenomatous tissue 3, which has increased the overall dimension of the gland and caused swelling thereof. The adenoma causes compression of the urethral lumen (urethra) 5, which extends through the two lateral lobes 1A, 1B of the prostate. The prostate 1 is surrounded by a capsule 7. Neuro-vascular bundles 9 are arranged on the exterior of the capsule 7 on two sides of the prostatic gland 1.

Any surgical treatment of BPH shall prevent damages to the capsule 7 and the neurovascular bundles 9, and possibly preserve the urethra for fast post-surgical recovery.

In FIGS. 1 and 2 reference number 10 designates cavities which are formed in the prostate 1 by vaporizing and sublimating adenomatous prostatic tissue using laser energy. The laser treatment can be performed by introducing one or more hollow needles or introducers in both lobes 1A, 1B of the prostate and by introducing an optical fiber through each needle, such that laser energy can be delivered to the interior of the adenomatous tissue causing vaporization thereof. The two lobes can be treated simultaneously. In other embodiments, each lobe can be treated separately from the other, i.e. the two lobes can be treated in sequence.

The needles and the optical fibers are introduced through the perineum, i.e. trans-perineally. The number of needles introduced in each lobe of the prostate 1 can depend upon the dimension of the prostate and upon the amount of adenomatous tissue to be removed. Two or more needles or introducers can be introduced at the same time in each lobe 1A, 1B of the prostate 1, such that adjacent or neighboring prostatic tissue volumes can be treated simultaneously. In other embodiments, one or more needles or introducers can be introduced in sequence in the prostatic tissue, for treating neighboring or adjacent volumes of the adenoma in timely shifted manner. This second approach will require a longer treatment time.

The number of simultaneously introduced needles can depend, inter alia, upon the number of laser sources available. It can be beneficial to provide as many independent laser sources as there are simultaneously operating optical fibers.

One or more needles or introducers and relevant optical fibers can be moved during treatment along the needle axis, such that subsequent tissue volumes can be illuminated with laser energy in a so-called pull-back procedure. With continuing reference to FIGS. 1 and 2, FIG. 3A, 3B, 3C illustrate a sectional view according to line III-III of FIG. 2, i.e. along a sagittal plane, in three different laser treatment steps of the prostate 1. In the exemplary embodiment of FIGS. 3A, 3B, 3C two introducers or needles 11, each guiding a respective optical fiber 13, are introduced in each lobe 1A, 1B of the prostate 1 through the trans-perineal route. The needles 11 are introduced through the perineum 15, i.e. through the area extending between the scrotum (not shown) and the anus 17.

Figure 3A:
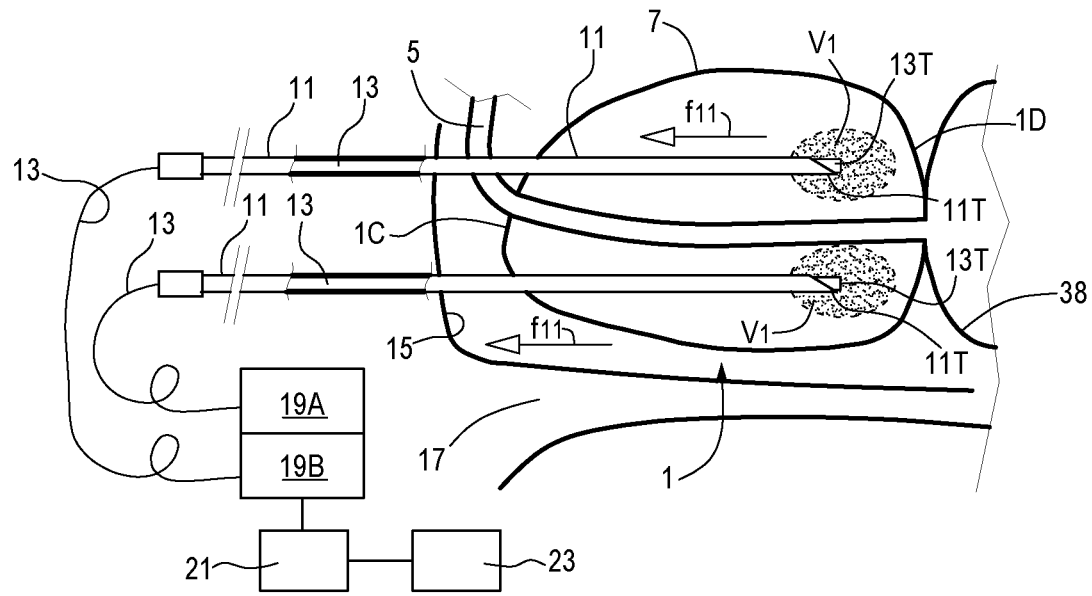
FIGS. 3A, 3B, 3C show sagittal cross-sectional views according to line of FIG. 2 during subsequent treatment steps.
Figure 3B:
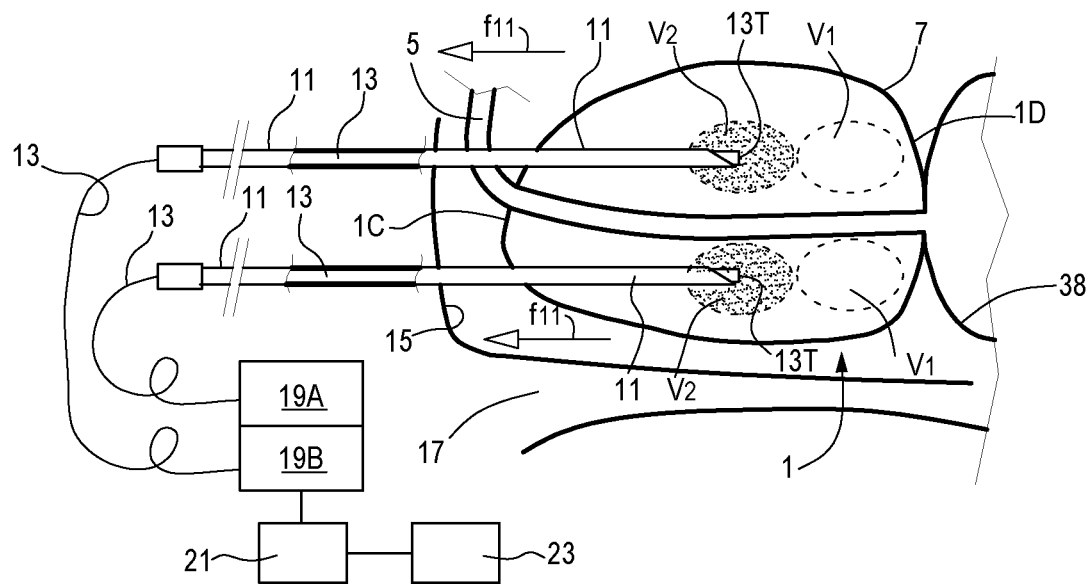
Figure 3C:
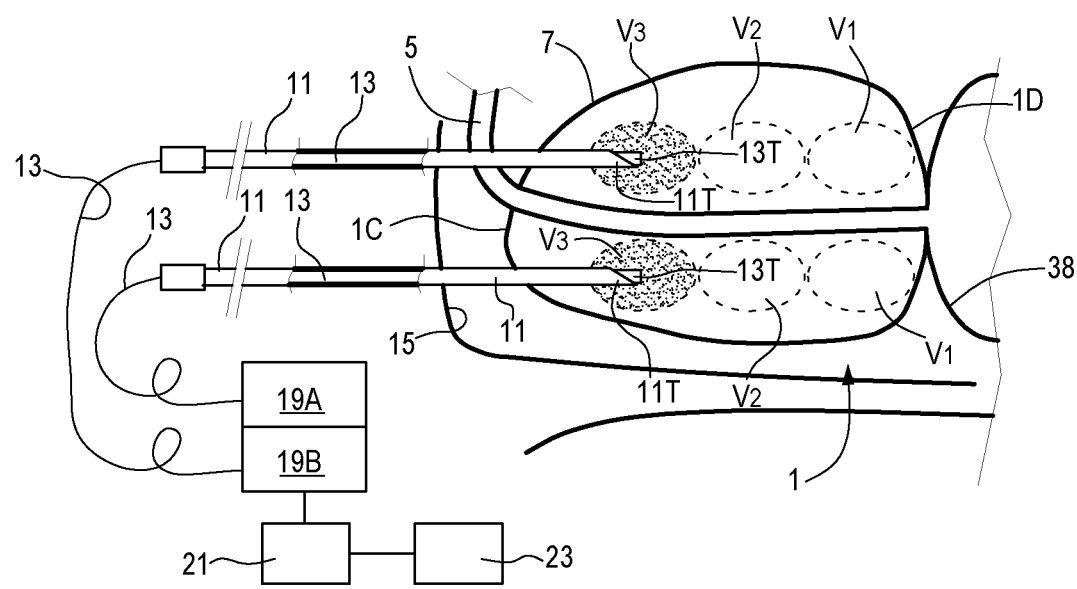

According to the embodiment shown in FIGS. 3A, 3B, 3C, each needle or introducer 11 and relevant optical fiber 13 are fully introduced in the prostate up to the starting position of FIG. 3A, where the treatment will initiate. This is the position where the needle tips 11T are farther away from the prostate apex 1C and nearest to the prostate base 1D and to the bladder floor. The bladder is labeled 38. Laser energy generated by a laser source is conveyed through the optical fibers 13 to the tips thereof, which are located at or near the tips 11T of the needles 11, or can project beyond said tips 11T.

As mentioned, according to some embodiments, independent laser sources can be provided for different optical fibers. In FIG. 3A one laser source 19A, 19B is shown for each optical fiber 13. Each laser source can be controlled independently from the others, such that for example each laser source can be turned on or off and the laser emission thereof can be adjusted independently from the others. For example the emission power, the emission time, the energy dose, the pulse frequency (in case of pulsed laser) can be adjusted for each source independently. In other embodiments each source can be coupled to multiple optical fibers. In some embodiments, different laser frequencies, i.e. sources emitting at different wavelengths can also be used in combination.

Insertion of the needles or introducers 11 and optical fibers 13, as well as their subsequent movement in the prostate can be performed with the aid of ultrasound imaging (US) using an ultrasound probe, for instance a rectal probe, as described in greater detail later on. In other embodiments, the insertion of the needles can be performed under magnetic resonance imaging in combination with non-magnetic introducers or needles 11, or using any other suitable imaging method.

Laser emission can be controlled by a control unit 21, which can be functionally connected to the laser sources 19A, 19B and to a user interface 23. As will be described in more detail here on, a controlled amount of laser energy is delivered by the laser source through the optical fibers 13 to cause vaporization and/or sublimation of tissue in a volume surrounding the tip of the optical fiber and/or in front of said tip. In FIG. 3A, V1 indicates the volume of adenomatous tissue which can be vaporized and sublimated by the laser radiation while the optical fiber tip is maintained in the position of FIG. 3A.

In order to remove a larger amount of tissue, the optical fiber 13 and the relevant hollow needle or introducer 11 can be gradually moved out of the patient's body. For instance, once the tissue volume V1 has been vaporized and/or sublimated by laser energy delivered through the optical fibers 13 in the first position of FIG. 3A, the needles 11 and relevant optical fibers 13 therein can be pulled back stepwise in an outward direction f11, in the position of FIG. 3B. The hollow needles 11 and optical fibers 13 can then be maintained in the new position of FIG. 3B for a given amount of time, during which laser radiation generated by the laser sources 19A, 19B irradiates the tissue in volume V2 and causes vaporization or sublimation thereof. Once the tissue in volume V2 has been vaporized and/or sublimated, the needles 11 and optical fibers 13 are moved a further step outward, until the position of FIG. 3C is achieved, where a third volume V3 of adenomatous tissue is vaporized or sublimated.

As can be appreciated from FIG. 3C, in a three-step process, two elongate volumes of adenomatous tissue have been removed by vaporization/sublimation along the pull-back motion trajectory of the two needles 11 in lobe 1A. The same operation can be performed simultaneously or subsequently in lobe 1B, such that at the end of the process, four volumes of tissue have been removed by vaporization and/or sublimation around the urethra 5. These four volumes are shown in a cross-sectional view in FIG. 2 and labeled V. The cavities thus formed will contract and thus immediately relieve pressure on the urethra 5. In contrast to so-called laser ablation techniques of the current art, which are based on tissue denaturation through laser radiation and subsequent removal of the denaturated/desiccated tissue through resorption, the treatment method of the present disclosure involves an immediate tissue volume reduction, with consequent immediate, real-time relieve of compressive forces exerted by the adenomatous tissues on the urethral lumen. The real-time effect of laser ablation by vaporization and/or sublimation of tissues through the transperineal route results in very fast recovery and short or no hospitalization.

As mentioned above, while in some embodiments all the needles 11 (four in the exemplary embodiment of FIGS. 2 and 3) are introduced at substantially the same time, such that four cavities 10 corresponding to the removed volumes V1, V2, V3 will form during the same treatment step, in other embodiments, the needles 11 and optical fibers 13 can be introduced in sequence, thus forming the cavities in two or more steps. For instance, the needles in one lobe 1A, 1B can be introduced first, and only upon completion of the treatment of the first lobe, needles will be introduced in the other lobe 1B, 1A. In other embodiments, a first step may involve insertion of one needle per lobe and a second step, to be performed upon completion of the first step, may involve insertion of the other needles in the two lobes.

Depending upon the dimension of the prostate 1 to be treated, a different number of hollow needles or introducers 11 and of optical fibers 13 can be used. In FIG. 1 two cavities 10 are formed by using just two needles 11, one per lobe 1A, 1B.

The dynamics of laser ablation by vaporization and/or sublimation with naked optical fibers involves the formation of a cavity of sublimated/vaporized tissue, surrounded by a small layer of vacuolated and dehydrated tissue. For a frontal-emission optical fiber 13 the cavity of vaporized tissue grows with respect to energy delivery time, i.e. as a direct function of the energy dose.

Figure 4:
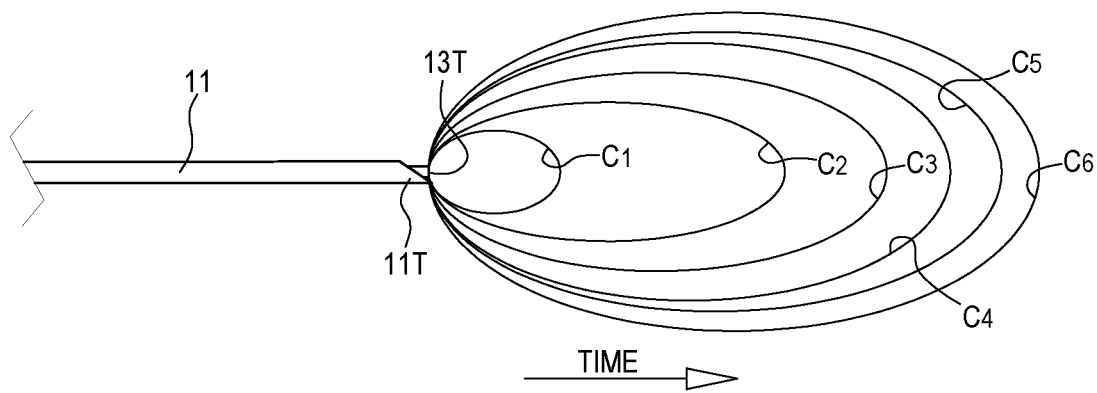
FIG. 4 illustrates a schematic of a cavity growing during tissue vaporization.

FIG. 4 pictorially illustrates cavity formation from the beginning to final saturated dimension. If the laser radiation intensity is above the tissue vaporization and sublimation threshold, a cavity C1 starts to form and grows in front of the fiber tip 13T. The laser energy is absorbed by the water contained in the tissue and causes vapor formation at the tip of the optical fiber 13.

In FIG. 4 the shape of the cavity is the one obtained with an optical fiber having a flat fiber tip, which produces a cavity of elliptic shape. As laser emission continues, the laser emission will further propagate through the empty volume formed by vaporization of the tissue such that the front of the tissue, i.e. the inner surface of the cavity, moves forward, away from the fiber tip. Tissue is, dehydrated and vaporized and finally sublimated in a cyclic way leading to a well-defined cavity in front of the fiber tip. As time proceeds, the cavity enlarges from C1 to C6.

As the volume of the cavity increases, the front velocity, i.e. the speed at which the surface of the cavity advances in front of the stationary fiber tip 13T moving away therefrom, decreases as pictorially represented by cavities C3, C4, C5, C6. The reason for this is that the energy per surface, which impinges on the forward moving cavity surface, reduces with the square of the distance from the fiber tip. The speed of ablation by vaporization and sublimation slows down until an asymptotic limit is achieved. When the cavity achieves the dimension represented by C6, whose size (length and the maximum diameter) depends on the chosen dose (duration of the treatment multiplied by the mean power value), the power density at the cavity margin is not able to sustain the process of vaporization and a stable condition is achieved in terms of removed volume, i.e. no further tissue can be vaporized and removed, such that the dimension of the cavity remains constant and the fiber is to be switched off.

When the dimension C6 is achieved, the needle or introducer 11 and the optical fiber 13 therein can be withdrawn stepwise with a pull-back maneuver as described above, such that an adjacent tissue volume can be treated in the next treatment step.

Since the parameters of the laser emission are chosen such that the irradiated tissue is removed by vaporization and sublimation, the relief of the compression exerted by the hypertrophic prostatic tissue on the urethral lumen 5 is rapidly obtained as can be understood from FIGS. 5 and 6. An additional brief rectal internal massage of the prostate operated by a finger can improve the effect by promoting or accelerating collapsing of the tissue around the cavity thus formed.

In FIG. 5 a schematic sectional view of the prostate 1 during or immediately after laser application is shown. One or more cavities 10 are generated by tissue vaporization and sublimation. In the exemplary embodiment of FIG. 5 five cavities 10 have been formed in each lobe 1A, 1B of the prostate 1. The tissue around the cavities 10 will collapse spontaneously or helped by a short rectal massage, such that the cavities 10 will shrink, as shown in FIG. 6. Shrinkage of the cavities causes a reduction of the external volume of the prostatic gland 1 and a reduction of the urethra compression. The urethra 5 re-opens as a direct consequence of the resulting pressure relieve thereon.

Figure 7:
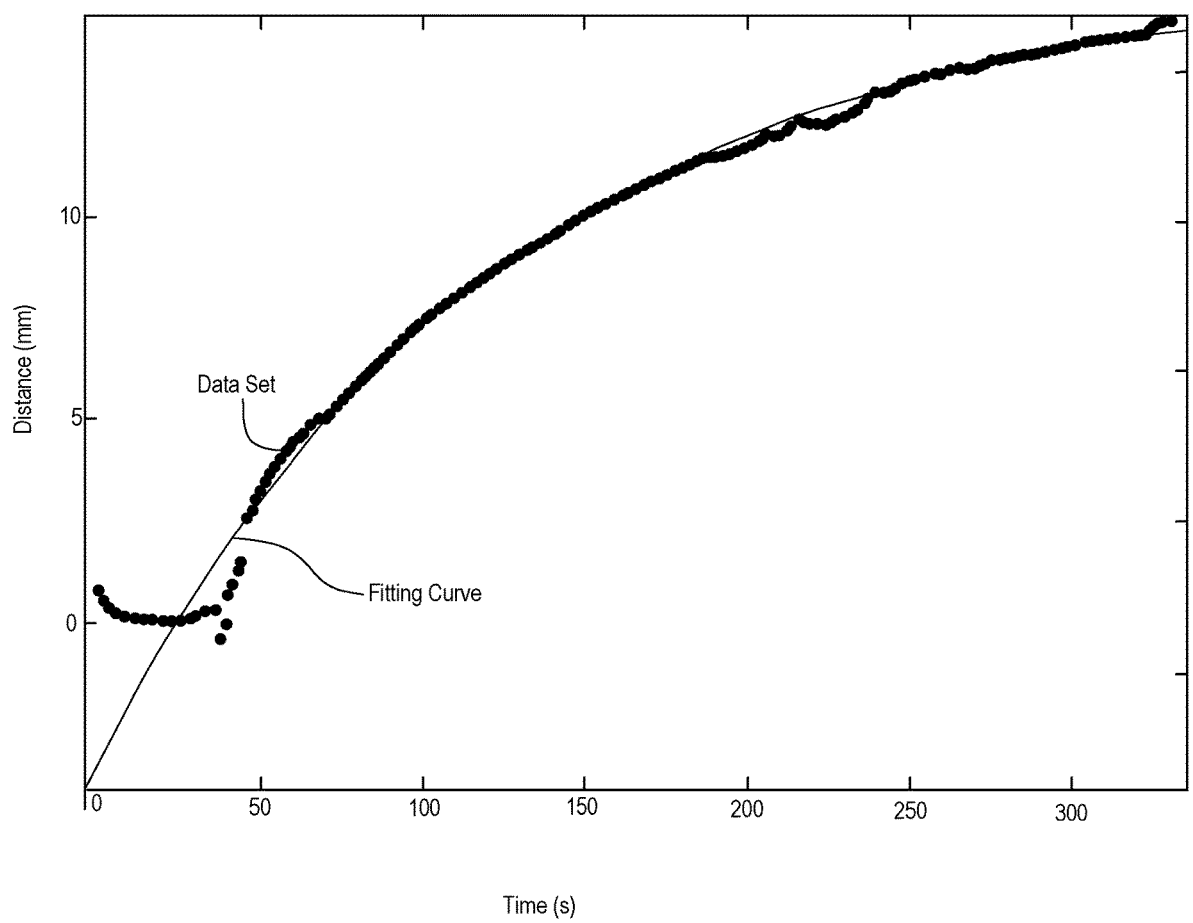
FIG. 7 illustrates a diagram showing the cavity volume increase during time.

From an experimental work ex vivo with an optical camera it was possible to measure the length (i.e. longitudinal dimension) of the cavity during its formation and the cavity dimension versus time could be plotted. FIG. 7 illustrates the cavity length vs. time. The dotted line represents the position (distance from the fiber tip) of the active front of the cavity. The continuous line is an exponential fitting curve of the raw data. Lasing starts at time 0. The data of FIG. 7 were obtained with a continuous laser beam with a power of 5 W, 1064 nm laser wavelength, conveyed through a quartz optical fiber with flat tip and a core diameter of 300 micrometer. The experimental data were obtained using a fresh porcine liver sample at room temperature.

At the beginning of the laser emission, for about 40 seconds, there is no movement in the forward direction, i.e. no cavity is formed in front of the fiber. This time is necessary to heat the tissue above 100° C. and activate intra and inter cellular water boiling and subsequent vapor formation in front of the fiber. If treatment stops before the vapor formation threshold is achieved, a spherical coagulated thermal lesion is created in the tissue, centered on the fiber tip. Once the vaporization threshold is achieved and exceeded, a cyclic action of dehydration, vaporization and sublimation occurs on new tissue layers facing the laser radiation emitted by the fiber tip. The active front of the cavity being formed moves forward in an asymptotic way (as described by the continuous fitting line in the graph of FIG. 7, up to saturation of the cavity length. This means that there is no further cavity enlargement even if energy delivery continues. This saturation phenomenon is dependent upon the slight divergence of the optical fiber emission. This means that the power density i.e. the radiation intensity decreases as the distance of the cavity surface from the fiber tip increases. In the asymptotic condition the power density decreases to a value that is under the vaporization threshold and hence the laser radiation is unable to induce further tissue removal. Once this condition is achieved, further energy delivered by the fiber is dissipated by thermal conduction to surrounding tissue and by blood perfusion.

The vaporization and sublimation threshold depends on the power intensity at the output of the optical fiber and therefore depends on the input power, the emission surface, and the dose, i.e. the amount of energy needed to give rise to the phenomenon. The wavelength also becomes important, because it determines the type of interaction between laser radiation and tissue. In particular the radiation absorption coefficient varies with the wavelength. For instance, for a laser radiation having a wavelength of 1064 nm, a power of 2 W (continuous wave) is sufficient to achieve tissue sublimation and vaporization and cavity formation with an optical fiber having a core diameter of 300 micrometers.

The lower power threshold to achieve vaporization and sublimation on a specific tissue depends on the power, energy delivery mode (continuous or pulsed), fiber tip (dimension and shape), absorption and scattering coefficients, which in turn depend on tissue and wavelength combination. The higher the power used, the faster the cavity formation speed. At 1064 nm the preferred power values are from 3 to 7 W in continuous wave mode.

The ratio between power and fiber tip surface defines the emitted radiation intensity. For 5 W delivered by a 300 micrometer core fiber diameter, the intensity is 17.7 W/mm$^2$. Intensities should be above 1 W/mm$^2$ to excite cavity formation with a 1064 nm wavelength and continuous wave with a dose of 1200-1800 J. With other laser wavelengths intensities are different and can be easily re-assessed.

Doses range from a few hundreds to a few thousands Joule. The optimal results are obtained from 600 J to 1800 J. There is a linear relationship between cavity volume and dose in this range. Doses greater than 1800 J induce a slight and not interesting increase in cavity enlargement.

According to some embodiments, for instance using a 5 W laser power and a wavelength of 1064 nm, the time required to start formation of a cavity in the tissue can be around 40 seconds, which correspond to an energy dose of 200 J. A first heating step precedes the actual tissue vaporization and cavity formation. The initial heating step is needed to bring the vaporization of water contained in the tissues. The first heating step is followed by cavity formation with a cavity volume which increases asymptotically. After a dose of 1800 J has been delivered (approximately 6 minutes) the maximum cavity volume has been achieved. Continued laser radiation with the fiber tip in the same position will not lead to any significant increase in the cavity volume.

The cavity formation process can be monitored by an ultrasound probe, exploiting the variable echogenicity of the tissues. During the first treatment step, preceding vaporization, the lased tissues will have a negligible echogenicity variation. The echogenicity will increase when vapor bubbles start developing. The echogenicity variations can be detected through an ultrasound probe. According to other embodiments, cavity formation can be monitored by Magnetic Resonance Imaging (MRI) or Computer Tomography (CT) imaging and can be detected as change in the tissue density. A combination of various imaging techniques is not ruled out.

Laser wavelengths that can be employed can be for instance those, which can be guided by optical fibers or wave guides usually in the visible and near infrared region. In some embodiments UV radiation can be used as well. According to the absorption spectrum, different wavelengths interact with different chromophores or water contained in the tissue. Thus, for each laser wavelength a set of lasing parameters should be evaluated in order to obtain tissue removal by vaporization and sublimation (i.e. vaporization and sublimation threshold should be evaluated for each configuration of lasing parameters in order to produce a cavity in a specific tissue). E.g. ablation parameters can be adjusted based upon the wavelength used. In some embodiments, a 10.6 μm laser radiation generated by a $CO_2$ laser source can also be used as waveguide are now available, which can guide also this radiation wavelength. According to other embodiments the following laser sources can be used: Nd:YAG laser emitting at 1064 nm; thulium laser emitting at 2010 nm; holmium lasers emitting at 2100 nm. Other suitable laser sources can include herbium laser at 2940 nm, using a hollow waveguide.

In some embodiments, different laser sources can be used in combination.

In some embodiments, the laser radiation can be continuous. In other embodiments a pulsed laser source can be used. Tests ex-vivo have been carried out with a pulsed holmium laser source using porcine liver tissue maintained at 20° C. (+1-5° C.) in a thermostatic bath. This temperature value was chosen with reference to the physiological in vivo value (about 37° C.). The operating temperature used during ex-vivo tests was reduced to 20° C. in order to take into consideration the absence of local blood perfusion which, in a living body, enables local heat removal during laser treatment. A holmium laser source with a wavelength of 2100 nm and pulsed emission was used in combination with a quartz optical fiber with a 550 micrometer core diameter.

Different pulse repetition frequencies and pulse amplitudes have been tested. Specifically, pulse repetition frequencies from 1 Hz to 20 Hz have been used, in combination with pulse amplitudes ranging from 0.2 Joule to 2 Joule. Different combinations of pulse repetition frequencies (PRF) and pulse amplitudes result in different power values. The following table summarizes different trials performed with different pulse repetition frequencies, pulse amplitude values, power, energy doses and treatment times (value in bold are constant for subgroup of experimental tests). The last column reports the dimensions of the cavity obtained in the liver tissue (length and width in millimeters):

| Sample | PRF | Pulse Energy | Power | Dose [Joule] | Exposure Time [s] | Cavity formation | Cavity dimension [mm × mm] |
|---|---|---|---|---|---|---|---|
| #1 | 20 Hz | 0.5 | 10 W | 1200 | 120 | Yes | 14 × 6 |
| #2 | 20 Hz | 0.5 | 10 W | 900 | 90 | Yes | 16 × 5 |
| #3 | 20 Hz | 0.5 | 10 W | 600 | 60 | Yes | 10 × 3 |
| #4 | 20 Hz | 0.5 | 10 W | 300 | 30 | Yes | 9 × 3 |
| #5 | 20 Hz | 0.5 | 10 W | 100 | 10 | Yes | 7 × 3 |
| #6 | 20 Hz | 0.4 | 8 W | 100 | 12.5 | Yes | 5 × 2 |
| #7 | 20 Hz | 0.3 | 6 W | 100 | 16.7 | Yes | 5 × 2 |
| #8 | 20 Hz | 0.2 | 4 W | 100 | 25 | Yes | 5 × 2 |
| #9 | 20 Hz | 0.4 | 8 W | 80 | 10 | Yes | 8 × 3 |
| #10 | 20 Hz | 0.3 | 6 W | 60 | 10 | Yes | 7 × 2 |
| #11 | 20 Hz | 0.2 | 4 W | 40 | 10 | No | NA |
| #17 | 5 Hz | 2 | 10 W | 100 | 10 | Yes | 8 × 3 |
| #13 | 15 Hz | 1 | 15 W | 100 | 6.7 | Yes | 6 × 2 |
| #12 | 15 Hz | 0.5 | 7.5 W | 100 | 13.3 | Yes | 7 × 2 |
| #14 | 10 Hz | 0.5 | 5 W | 100 | 20 | Yes | 8 × 2 |
| #16 | 5 Hz | 0.5 | 2.5 W | 100 | 40 | Yes | 6 × 2 |
| #15 | 1 Hz | 0.5 | 0.5 W | 100 | 200 | No | NA |

According to exemplary embodiments of the laser ablation method disclosed herein, the emission parameters may be maintained constant during the entire treatment time. However, this may not always be possible or preferred. In some embodiments, the laser ablation treatment can be performed with a gradually increasing emission power, for instance to prevent tissue explosion due to abrupt vapor formation. In other embodiments, higher power values can be used at the beginning of the treatment, before the tissue cavity starts forming, followed by lower power emission, which can be used to promote hemostasis.

When pulsed laser emissions are used, the pulse repetition frequency, or pulse repetition rate, and the energy per pulse can be used as further selectable and adjustable parameters. The same mean power can be indeed achieved with different combinations of pulse repetition rates and energy per pulse. However highly energetic pulses with a low pulse repetition rate will have a different effect on the treated tissue than pulses having a lower energy but a higher repetition rate.

As mentioned, the method involves the use of one or more fibers 13 that are trans-perineally introduced in the prostate by means of thin needles or introducers 11. The more fibers are placed inside the lobes 1A, 1B of the prostate 1 the quicker and more effective the treatment will be. The optimal trade-off between effectiveness and time duration consists of simultaneous energy delivery, which involves one or two fibers 13 and respective introducers 11 per lobe (thus from two to four optical fibers 13 for the whole gland) as shown in FIG. 2. However, a smaller number of fibers (FIG. 1) or a larger number of fibers (FIGS. 5 and 6) can be used.

Two or more adjacent cavities may merge into a single cavity, if so desired. The treatment can also be performed with a single fiber and with multiple illuminations and repositioning.

According to the cavity shape, which depends upon several parameters, such as shape of the fiber tip, power, dose, absorption coefficient, it is possible to define safety criteria for the fiber tip positioning. As a matter of fact, the fiber tip can be placed at a safety distance from critical structures inside, around and adjacent the prostate 1, such as the urethral lumen 5 inside the prostate 1, the capsule 7 around the prostate 1 and the two neurovascular bundles 9 outside and adjacent the prostate 1.

According to some embodiments, using a 3 W continuous wave power with a flat tip optical fiber the following safety rules can be applied: lateral distance equal to or larger than 5 mm (optimal distance 10 mm); front distance between the fiber tip and the capsule 7, at least 15 mm. Higher power can be used with redefinition of the safety criteria. Higher power levels generate longer cavities. Thus, a larger safety distance between the fiber tip and the prostate base 1D (front distance between capsule and fiber tip) should be adopted.

The mutual distance between fibers 13 depends on how many cavities C are planned to be formed in the tissue. Usually said mutual distance ranges between 5 mm and 15 mm depending upon total prostate volume and other constrains imposed by the above mentioned safety criteria (distance from capsule and urethra, for instance).

At 5 W power, safety distances should be re-assessed, especially as far as the front distance, i.e. the distance between the capsule and the fiber tip is concerned.

Depending on the prostate volume and in particular the longitudinal length, from base to apex, it is possible to gradually and stepwise withdraw the needles 11 and optical fibers 13 and perform a laser radiation at each newly reached position (pull-back maneuver), as described above in connection with FIGS. 3A-3C. This allows maximizing volume removal with a single needle insertion. The extension of each withdrawal movement, i.e. the length of the needle 11 and the fiber 13 which is extracted from the prostate 1 at each pull-back maneuver, can be assessed by the aid of an ultrasound or magnetic resonance imaging system or by ticks on the needle cannula.

In some embodiments, the treatment can start with the fiber tips positioned at 15 mm from the capsule (prostate base) in the front direction and after a first energy delivery, if the apex-to-base distance allows it, the needle can be pulled back and a new dose of laser energy can be delivered in the new fiber position. The number of pull-back movements is related to the apex-base dimension of the gland 1. The greater the number of pull-back steps, the greater the amount of tissue removed from the gland 1. For each insertion of the fibers the treatment stops when it is not possible to withdraw the fiber further, based on the safety rule, as the minimum distance between capsule and fiber tip must be respected.

The method can be carried out with optical fibers having a flat tip. In other embodiments, however, special optical fibers, having a different geometry, can be used. Special optical fibers may have a special tip shape obtained by chemical etching, mechanical lapping, thermal fusion or other chemical, physical or mechanical treatment.

In some embodiments, the optical fiber may be adapted to achieve side firing or globular firing. As used herein, the term "side firing optical fiber" can be understood as an optical fiber which emits at least one optical beam from the side surface thereof. As used herein, the term "globular firing optical fiber" can be understood as a fiber having a tip shaped such as to generate a substantially globular or spherical emission.

Figure 8:
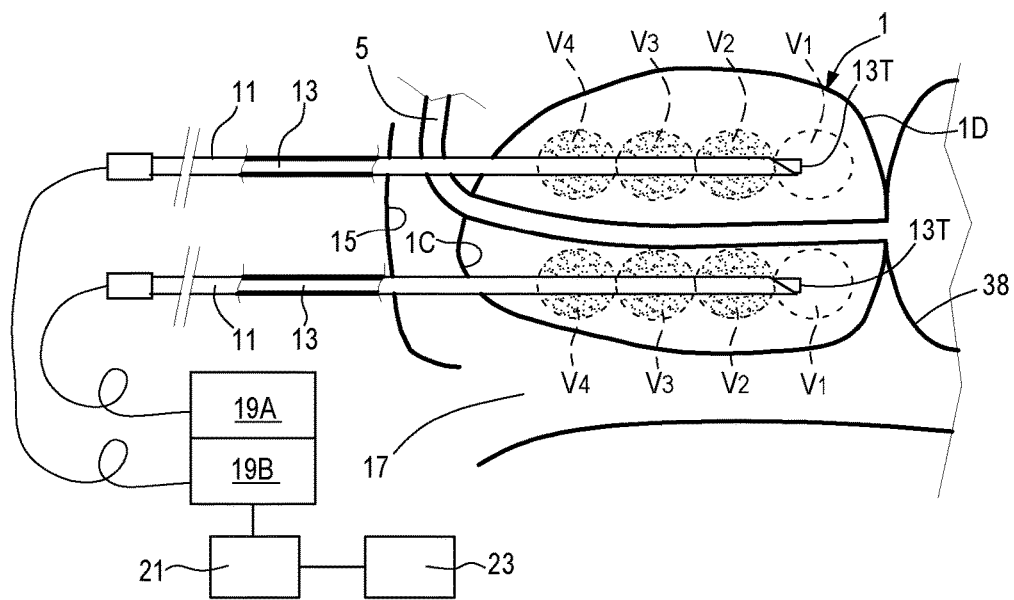
FIG. 8 illustrates a view similar to FIGS. 3A-3B-3C of a further embodiment.

In some embodiments, globular firing can be obtained with an optical fiber having a conical tip, rather than a flat, planar tip. A globular firing optical fiber can generate substantially spherical cavities in the tissue. FIG. 8 schematically illustrates a cross sectional view according to a sagittal plane of a prostate 1 under treatment, similar to FIGS. 3A-3C. The same elements are labeled with the same reference numbers as in FIGS. 3A-3C and will not be described again. In the embodiment of FIG. 8 the optical fiber tip 13T is shaped such as to have a globular, i.e. substantially spherical emission, which generates a substantially isotropic energy distribution on a spherical surface. This results in a spherical volume V1 of tissue vaporization and sublimation and consequently generates a substantially spherical cavity. V2, V3, V4 indicate ablation volumes which are obtained in subsequent pull-back steps, during which the introducers 11 and the optical fibers 13 guided therein are gradually withdrawn from the prostate 1.

The mechanism of tissue removal remains the same as described above. The cyclic dehydration, vaporization and sublimation process takes place on enlarging spherical surfaces due to isotropic energy deliver energy. Spherical cavities are more suitable for treatments in small organs and close to critical vital structures, because of the geometrical shape of the spherical cavity formed, the surface whereof is maintained at substantially the same distance from the fiber tip 13T in all directions. In other words, the shape of the cavity generated by laser vaporization or sublimation of the tissues is not related to the direction of insertion of the needles, contrary to what happens when optical fibers with a flat tip are used, which generate elliptic cavities.

Also with globular firing optical fibers laser power and energy can be set at 3 W and 1800 J, respectively, for a 1064 nm wavelength laser source operating in a continuous wave mode. In this case, the above mentioned safety rules setting the minimum distances between the tips of the optical fibers and the critical structures inside, around and outside the prostate must be adapted to the new shape of the cavity that is produced. In some embodiments using a globular (spherical) firing optical fiber with a 5 W laser source, the tip 13T of each optical fiber 13 should be at least 1 cm from the critical structures (urethra, capsule) even in the transverse direction.

The use of isotropic or quasi-isotropic radiators (optical fiber tips 13T) allows using higher power ranges than those which can be applied using free handle flat-tip optical fibers. The safety distances between fiber tip and critical structures of the prostate should be reassessed for each case.

Figure 9:
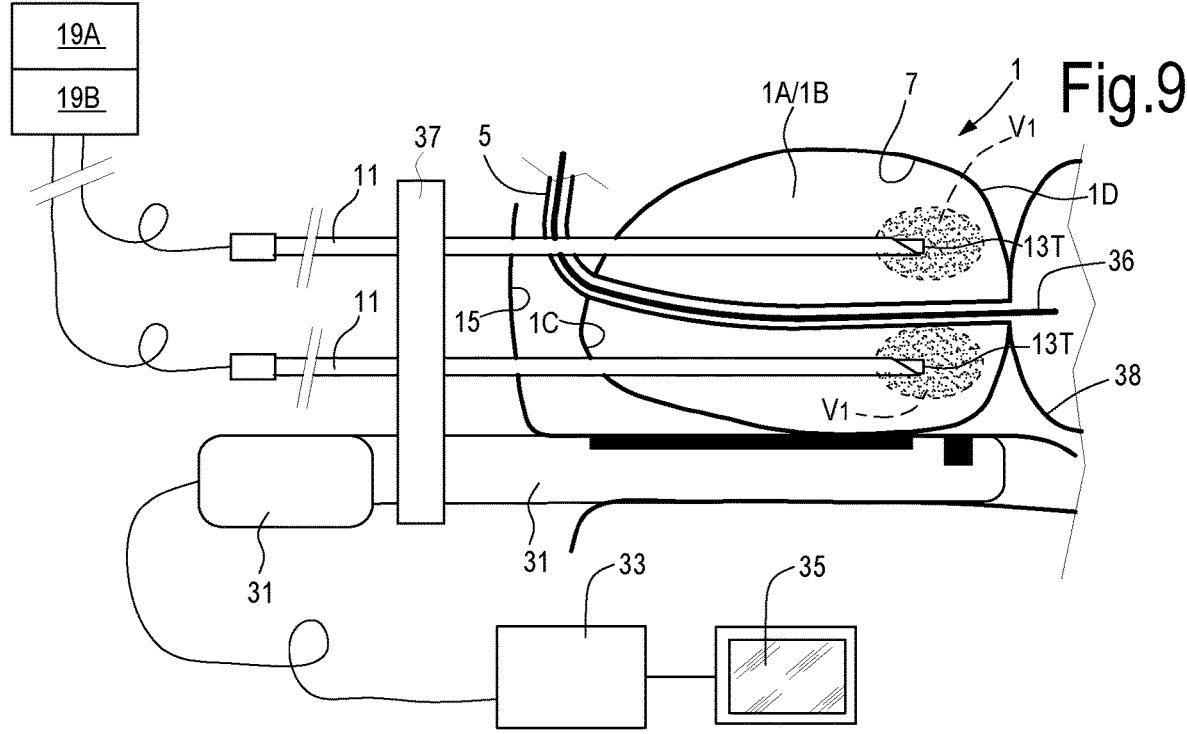
FIG. 9 illustrates a sagittal cross-sectional view of a prostate during treatment with trans-rectal ultra-sound (US) imaging guidance.

As mentioned above, positioning of the needles or introducers 11 can be performed under imaging guidance, for instance under ultrasound guidance preferably with a trans-rectal probe and preferably with a bi-plane probe. A bi-plane probe allows displaying images according to transverse and longitudinal (sagittal) planes of the prostatic gland. FIG. 9 shows a sectional view according to a sagittal plane of a prostate during insertion of two needles 11 in one of the lobes 1A, 1B of the prostate 1, using US (ultrasound) imaging guidance. An ultrasound (US) trans-rectal probe 31 can be inserted into the rectum and allows imaging the portion of interest. The US trans-rectal probe 31 can be connected to an ultrasound imager 33, which can be provided with a display 35. The trans-perineal insertion of the needles or introducers 11 can be performed freehand or through a needle guide device 37 connect to the trans-rectal probe 31.

The US trans-rectal probe 31 can be maintained in place also after insertion of the needles 11 and optical fibers 13, during part of the treatment or during the entire treatment. Ultrasound imaging can be used to control whether tissue vaporization or sublimation and the formation of the cavity in the gland tissue proceeds correctly. Additionally, in case of pull-back maneuver, as described above in connection with FIGS. 3A, 3B, 3C, US imaging can assist the operator to retract the needles 11 by the required length at each pull-back step, such that subsequently removed tissue volumes merge in a single, longitudinally extending empty cavity formed in the gland tissue.

A catheter 36 can be placed into the urethra up to the bladder 38 prior to start treatment of the prostate 1, to provide a reference point in the US image shown on the display 35.

In some embodiments of the method disclosed herein, removal of gaseous by-products, generated by vaporization and/or sublimation of the lased gland tissues may be particularly beneficial. Removing gaseous by-products generated by interaction of the laser radiation with the gland tissue may promote and facilitate the entire tissue removal process. Vapor or other side products which are not removed are otherwise slowly absorbed by microcirculation and blood perfusion, a process which takes some time until complete elimination is obtained. Removal of the vapor or other side products through the needles during lasing or after lasing but prior to removing the needles from the prostate can substantially accelerate the reduction of the prostate volume and thus the relieve of the pressure applied by the prostatic tissue on the urethra 5.

During lasing and gas formation caused by tissue vaporization or sublimation, a positive pressure is generated inside the cavity formed by the laser radiation. The gas can flow through an annular gap between the optical fiber 13 and the inner surface of the needle 11, thus escaping from the needle hub. For this reason, according to some embodiments, the coupling between needle hub and optical fiber hub is keep opened. In other embodiments, selectively closable and openable ports can be provided, for gas or vapor venting purposes. A possible coupling system with grooves for gas discharge is disclosed in U.S. Pat. No. 8,265,446, the content whereof is entirely incorporated herein by reference.

According to some embodiments, improved removal capability of the needle shaft or introducer cannula 11 can be achieved by providing side holes or ports in the wall of the needle close to the tip thereof. These side holes or ports can prevent obstruction of the main channel of the needle in case solid particles and debris are present in the cavity generated by laser radiation.

FIGS. 10 and 10A schematically illustrate a needle or introducer 11 with a needle hub 11A and a needle tip 11T. An optical fiber 13 is introduced through the needle 11 and the emitting fiber tip 13T is located in a cavity being formed by lasing the surrounding prostatic tissue. The cavity C contains pressurized vapor or gaseous side-products generated by the vaporization or sublimation of the tissue. The gas escapes through the annular gap between the optical fiber 13 and the inner surface of the needle 11. The fiber hub is shown at 13A and at least one venting port is available between the fiber hub 13A and the needle hub 11A, such that gas G can escape from the cavity C. In FIG. 10A, which shows an enlargement of the needle and fiber tip area, side holes 11H near the needle tip 11T are provided, which facilitate gas or vapor removal, should the end of the needle become clogged by solid or high-density liquid debris.

In some embodiments, improved efficiency can be achieved by promoting gas and vapor extraction from the cavity being formed in the prostate tissue. According to some embodiments, a pressure reduction can be generated in the interior of the needles 11, for instance by means of a suction device, such as a vacuum pump or the like.

With continuing reference to FIG. 10, in FIG. 11 a vacuum pump 41 is fluidly coupled to the interior of the needle 11. The pump 41 is adapted remove gas or vapor by depressurizing the interior of the needle, and more specifically the annular gap between the needle 11 and the optical fiber 13. The negative pressure in the needle 11 can be enough to aspirate gas or vapor from the cavity C being formed by the laser radiation in the prostate tissue, such that the pressure in the cavity C is maintained under control. A first duct 43 can fluidly couple the interior of the needle 11 to a collecting tank 46. The latter can be fluidly coupled to the vacuum pump 41 through a duct 45. Particles or condensed vapor can be collected in the tank 44 and prevented from reaching the vacuum pump 41.

According to further exemplary embodiments, a double way introducer or needle 11 can be used, in order to apply suction to a first passageway and refill the cavity under formation with fresh air through the second passageway. This can be beneficial in order to fully remove from the cavity C gases or vapors that can interfere with the laser radiation, thus decreasing the effectiveness of laser-to-tissue interaction.

Figure 12:
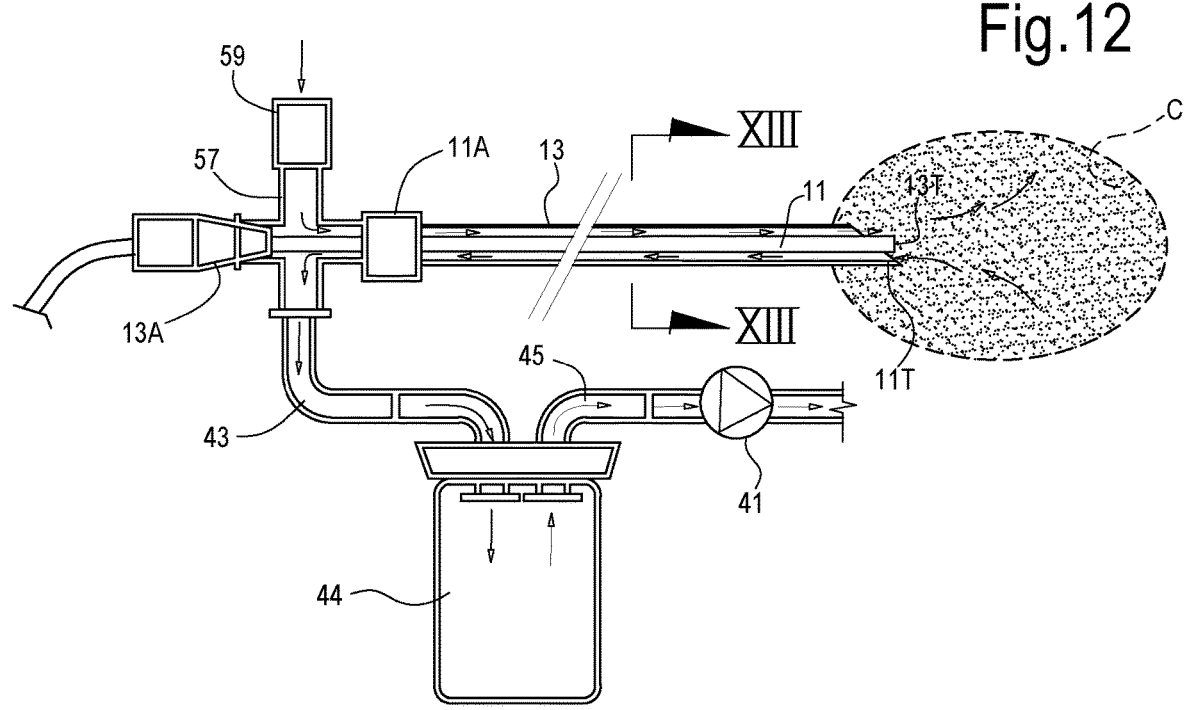
Figure 13:
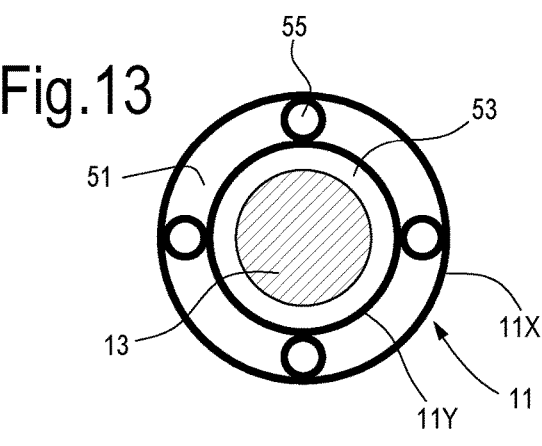
FIGS. 13 and 14 illustrate cross-sectional views according to line XIII-XIII of FIG. 12 in two exemplar embodiments.
Figure 14:
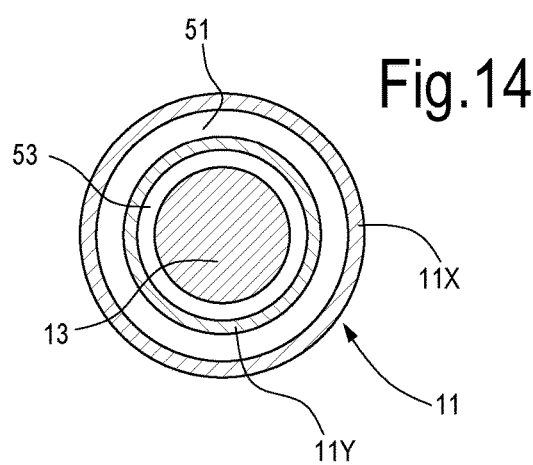

With continuing reference to FIGS. 10 and 11, FIG. 12 illustrates an embodiment wherein a two-way introducer or needle 11 is used in combination with suction and fresh air feeding inside the cavity C being formed during laser vaporization or sublimation of the lased prostate tissue. The same reference numbers used in the previous figures designate the same or corresponding parts or elements, which are not described again. FIGS. 13 and 14 illustrate cross-sectional views according to line XIII-XIII of FIG. 12, of two exemplary embodiments of a two-way needle or inserter 11. The needle 11 may comprise an external cannula 11X and an internal tubular element 11Y. The optical fiber 13 can be housed in the internal tubular element 11Y in a substantially coaxial position therewith. In some embodiments (FIG. 13) distancing and centering members 55 can be arranged between the cannula 11X and the inner tubular element 11Y. A first annular passageway 51 is thus formed between the cannula 11X and the inner tubular element 11Y. A second annular passageway 53 is formed between the inner tubular element 11Y and the optical fiber 13.

Referring to FIG. 12, a duct 57 can be in fluid communication with the environment and with the first pathway 53. An air filter 59 can prevent pollutants, and pathogens, such as micro-organisms, from entering the needle passageway 53. The second passageway 53 is fluidly coupled to the duct 43 and thus, through the collector tank 44 and the duct 45, with the suction or vacuum pump 41.

The device illustrated in FIGS. 12, 13, 14 operates as follows. Once the needle 11 has been placed in the correct position inside the prostate, possibly with the aid of US imaging or other imaging facility, the laser source is activated and laser radiation interacts with the tissue surrounding the tip 13T of the optical fiber 13, causing vaporization and/or sublimation of the tissue and thus forming a cavity C of gradually increasing volume. The vacuum pump 41 removes gaseous matter from the cavity C under formation through the second pathway 53 of the needle, and the negative pressure generated in the cavity C causes fresh air to enter the cavity through the air filter 59, the duct 57 and the first passageway 51 of the needle 11. The gaseous matter removal and air circulation can continue for the entire cavity formation step, such that the cavity C will be free or substantially free of laser absorbing gaseous side products generated by laser-tissue interaction. This may be beneficial in terms of speed of treatment and dimension of the cavity C obtained for each position of the needle or introducer 11.

According to yet further embodiments, enhanced BPH treatment results can be achieved by combining tissue ablation through vaporization with a mechanical action through the urethra 5. In some exemplary embodiments, an inflatable balloon can be introduced in the urethral lumen 5 of the patient prior, during or after insertion of the needles 11.

With continuing reference to FIGS. 1 to 14, FIGS. 15A, 15B and 15C illustrate a cross sectional view along a sagittal plane of the prostate during treatment with optical fibers introduced trans-perineally in the prostate and one or more inflatable balloons placed in the urethra 5.

Figure 15A:
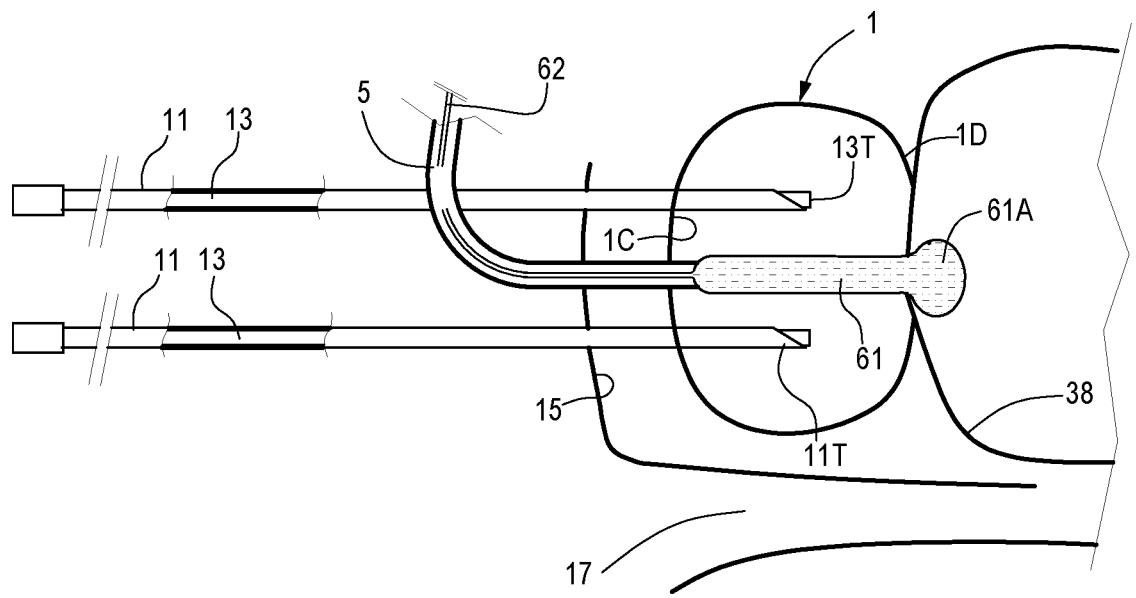
FIGS. 15A. 15B and 15C illustrate cross-sectional views according to a sagittal plane in a further embodiment.

In FIG. 15A an elongated inflatable balloon 61 has been positioned in the urethra 5 of the patient by means of a catheter 62 or through any other suitable means. Once the balloon 61 is placed in the correct position, it can be inflated, for instance with a physiologic solution at suitable pressure and temperature conditions. Inflatable balloons for angioplasty or similar surgical applications are known, and they can be adapted for use in the method disclosed herein.

Upon inflation, the balloon 61 causes compression of the surrounding tissue of the prostatic gland and dilation of the urethra 5 at its physiologically normal conditions, or even beyond the physiologically normal dimension of the urethral lumen 5. Compression of the surrounding tissues can facilitate evacuation of the gaseous or vapor by-products generated by laser-tissue interaction and tissue vaporization or sublimation.

In addition, due to a thermo-plastic effect, once the balloon 61 is deflated and removed from the urethra 5, the surrounding tissues will at least partly maintain their compressed condition, thus providing more efficient relief to the urethra 5 immediately after treatment.

In some embodiments, the filling fluid used to inflate the balloon 61 can be circulated, to maintain the fluid temperature under control. In some embodiments, the fluid temperature can be maintained above basal temperature, e.g. around 40-42° C. In other embodiments, the fluid temperature can be maintained at a lower temperature, even below the body temperature. Temperature control and fluid circulation can be used to cool the urethra 5 and the tissue immediately surrounding the urethra, preventing damages due to overheating.

In the embodiment of FIG. 15A a single balloon 61 with an enlarged head end 61A is retained in the correct position by introducing the balloon 61 in the urethra 5 until the head end 61A thereof reaches the bladder 38.

Figure 15B:
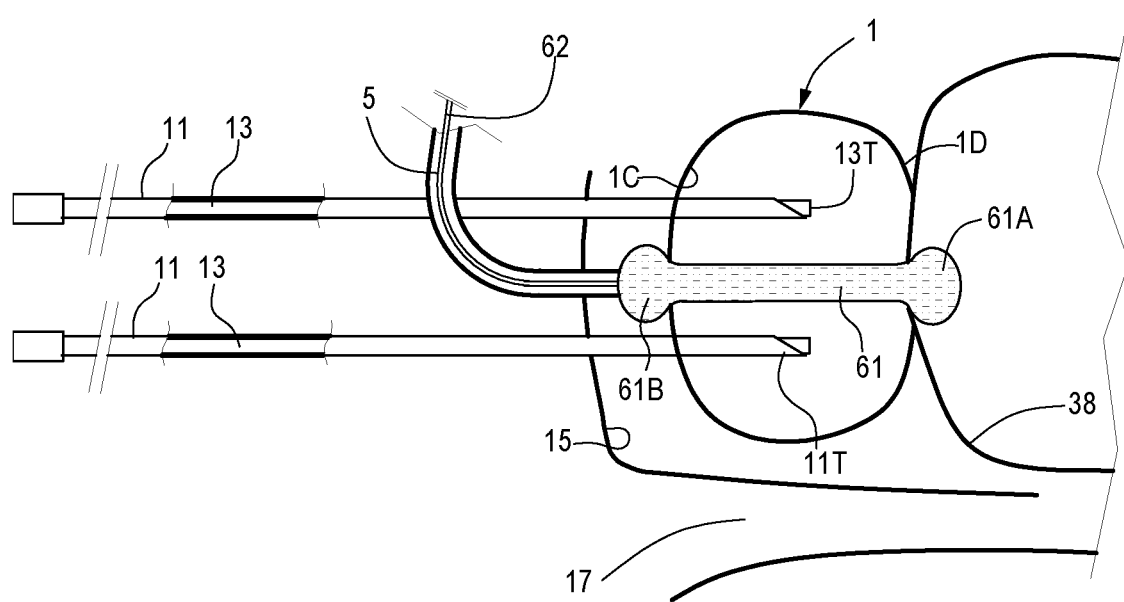

In FIG. 15B, with continuing reference to FIGS. 1-15A, an inflatable balloon 61 is used, which has an elongated central body and two expanded ends 61A, 61B. These latter provide for a precise and correct positioning of the balloon 61 in the urethra 5 and contribute in maintaining the inflated balloon 61 in the correct position during lasing of the prostate 1.

Figure 15C:
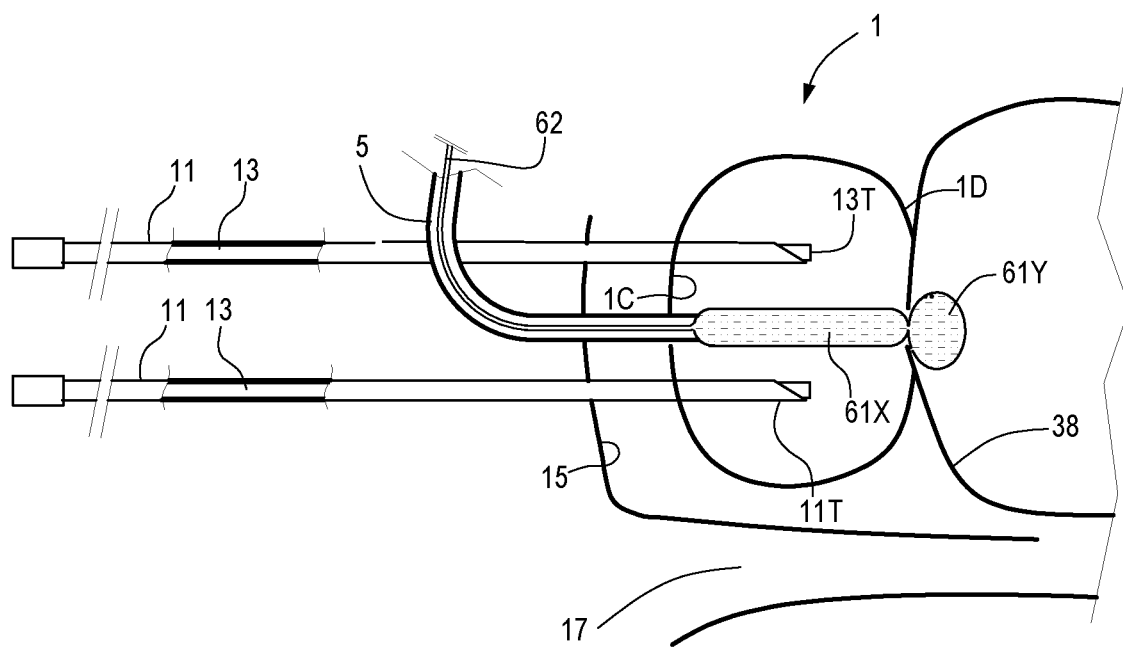

In FIG. 15C, with continuing reference to FIGS. 1-15B, two inflatable balloons 61X, 61Y are used in combination with one another. The first balloon 61X can be introduced in the bladder 38 and the second balloon 61Y can be positioned in the urethra 5. The two balloons 61X, 61Y can be introduced by means of the same catheter 61 and the balloon 61X provides for safe positioning of the second balloon 61Y in the urethra 5.

Balloons 61 of different shapes and/or dimensions can be selected by the operator based upon the dimension of the prostate 1 to be treated, the anatomic features of the patients, or other factors.

Figure 16:
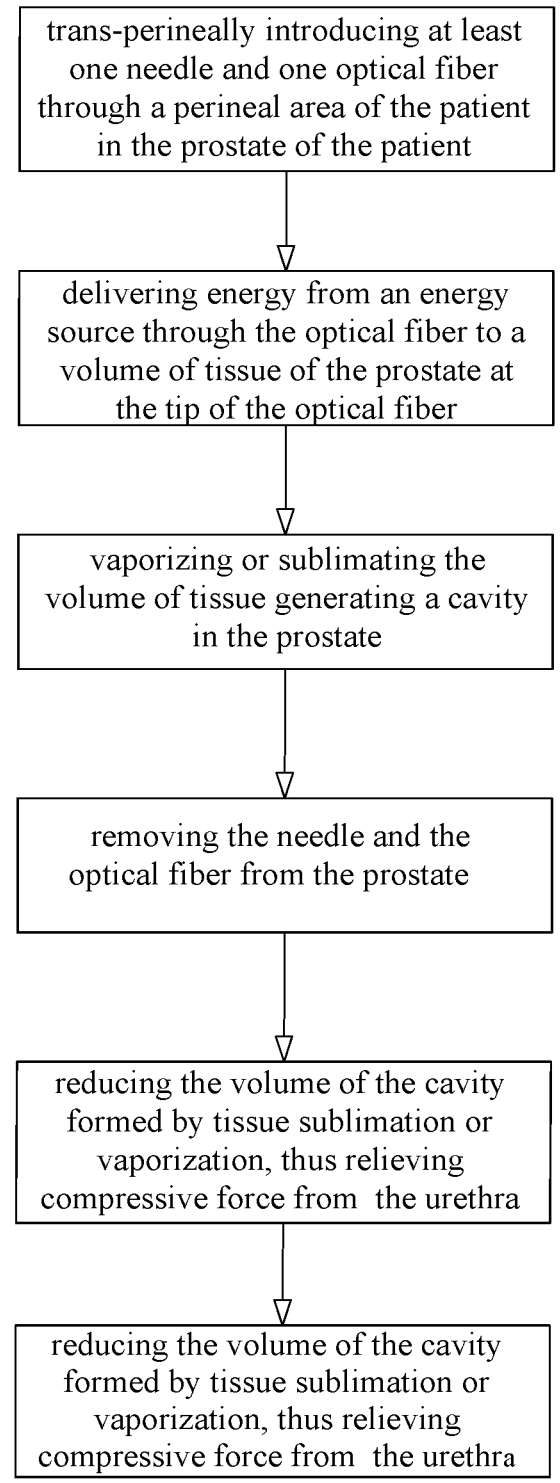
FIGS. 16, 17 and 18 illustrate flow-charts summarizing the main steps of BPH treatment methods according to the present disclosure.
Figure 17:
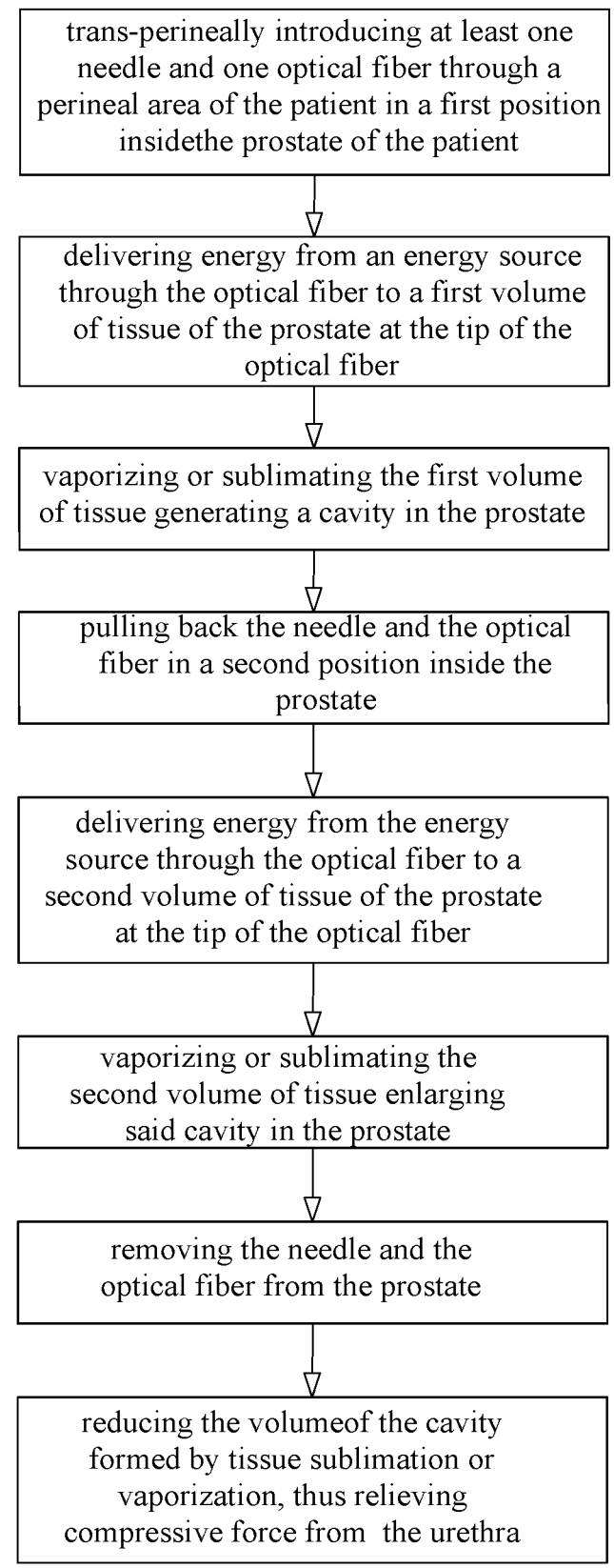
Figure 18:
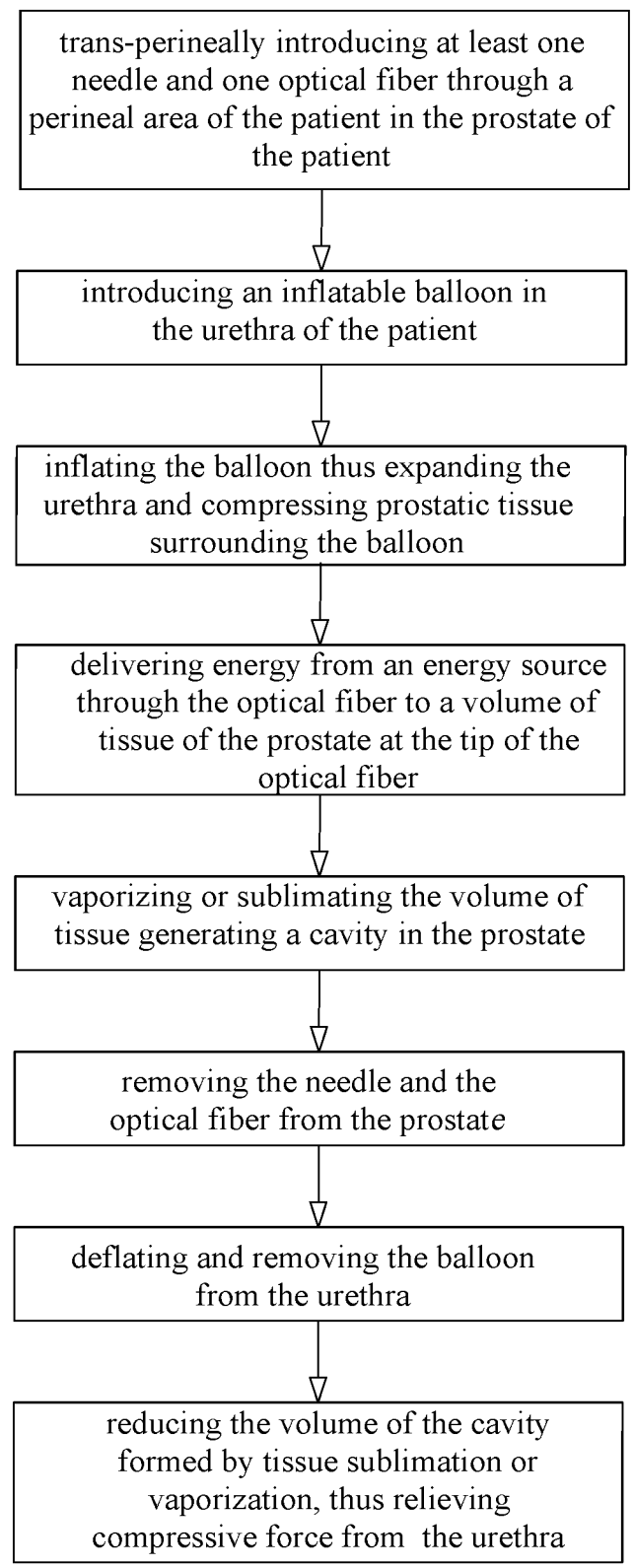

FIGS. 16, 17 and 18 show three flow-charts which summarize exemplary methods of treating BPH disclosed herein.

In some embodiments, treatment safety can be increased by adding temperature control facilities, for instance, aimed at preventing over-heating of critical structures inside or around the prostate 1 under treatment.

Figure 19:
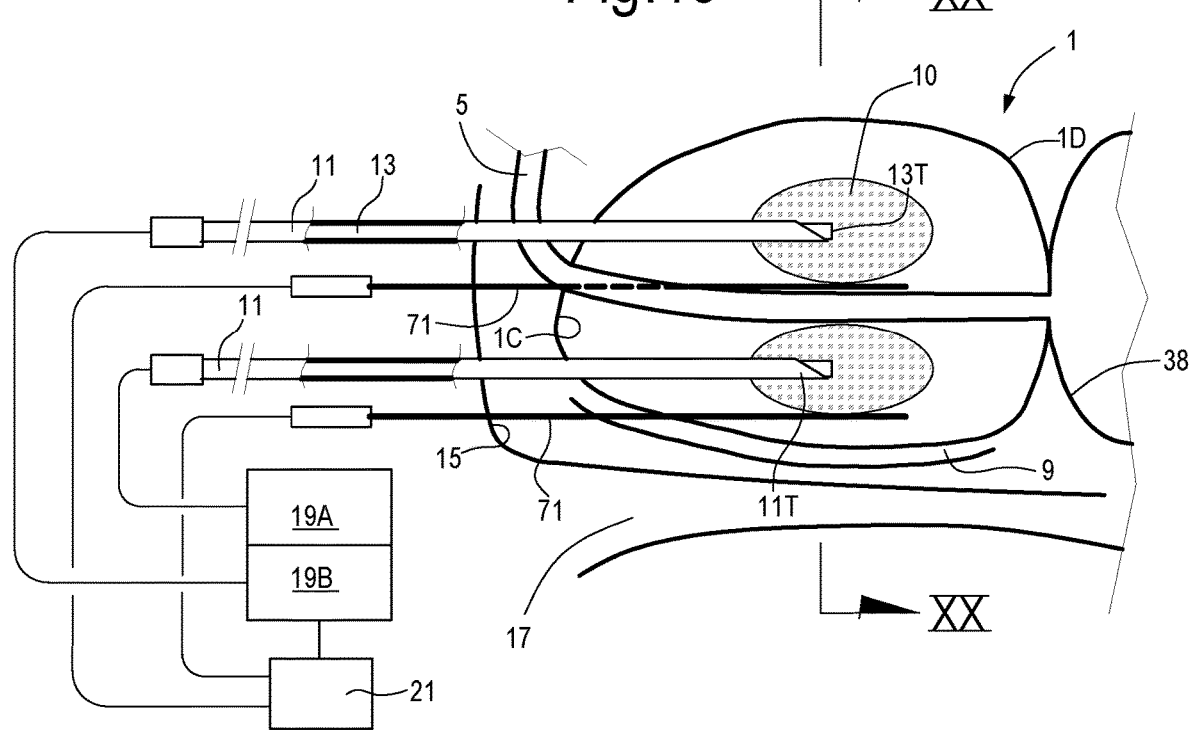
FIG. 19 illustrates a cross sectional view according to a sagittal plane of a prostate under treatment with the use of temperature sensors.
Figure 20:
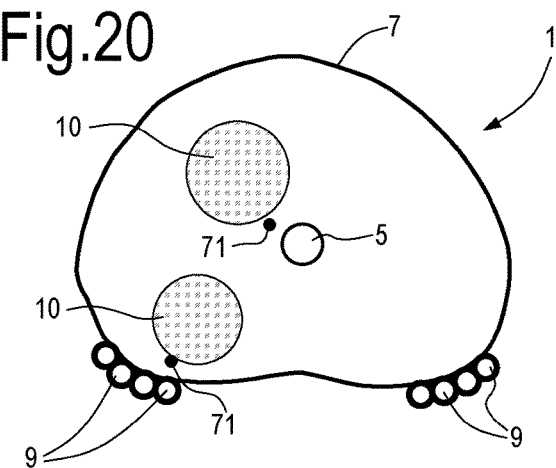
FIG. 20 illustrates a cross sectional view according to line XX-XX of FIG. 19.

Referring to FIGS. 19 and 20, with continuing reference to FIGS. 1 to 15C, temperature sensing arrangements 71 can be introduced in the prostate 1 under treatment in combination with needles 11 and optical fibers 13. Thermocouples, thermoresistors or temperature measuring fibers can be introduced through needles or cannulae in the prostate. In FIGS. 19 and 20 reference number 71 indicates any possible kind of temperature measurement device, apparatus or arrangement. For instance, a pervious needle or a cannula can be used to introduce a thermocouple or a thermoresistor near critical areas of the prostate 1. In some embodiments an optical fiber with a Bragg grating can be used instead of, or in combination with thermocouples and/or thermoresistors.

In some embodiments, the temperature sensitive portion of the temperature sensing arrangement can be located at or near the tip of the temperature measuring device 71. In other embodiments, temperature sensing areas can be located in several positions along the axial extension of the temperature measuring device 71, for example if optical fibers with a Bragg grating are used. These latter are able to detect the temperature at different depths in the prostate, for example parallel to the axial extension of the needles 11.

In FIGS. 19 and 20 two temperature sensing or measuring devices 71 are introduced in the prostate 1. A first temperature sensing or measuring device 71 is positioned between the urethra 5 and the area where a first cavity 10 will be generated by a first optical fiber 13. A second temperature sensing or measuring device 71 is arranged between the neuro-vascular bundle 9 and the area where a second cavity 10 will be generated by a second optical fiber 13. Thermal damages of the urethra 5 and of the neuro-vascular bundles 9, due to over-heating or excessive laser radiation, can thus be prevented. The temperature measuring or sensing devices 71 can be functionally coupled to the control unit 21, such that the emission parameters of the laser sources 19A, 19B can be modulated automatically to maintain the tissue temperature under control and prevent thermal damages of critical structures in and around the prostatic gland 1. For instance the control unit 21 can be adapted to reduce the mean power, or the peak pulse energy, or other laser emission parameters, if the temperature measured by at least one of the temperature sensing or measuring devices 71 increases above a given safety threshold. In some embodiments, one or more temperature sensing or measuring devices 71 can be combined with some or each one of the optical fibers 13, such that each or some of the laser sources 19A, 19B can be automatically controlled through data from the temperature sensing or measuring devices 71 combined with the respective optical fibers 13.

In other embodiments, temperature information from the temperature sensing or measuring devices 71 can be made available to the operator, for instance through a suitable user interface, such as a display or monitor. The operator will then manually modify the laser emission parameters based on the temperature information from the temperature sensing or measuring devices 71.

According to a further aspect, the disclosure also concerns a method of reducing a volume of a benign or malign tumor in an organ of a patient in need of said treatment. According to a yet further aspect, the disclosure concerns a method for removing tissue from an organ of a patient according to a mini-invasive technique.

According to some embodiments, the method comprises the following steps. A first step involves the introduction of at least one energy delivery device in a first position in an organ of the patient. The energy delivery device can include an optical fiber coupled to a laser source. The optical fiber can be introduced through a needle or introducer. Once the energy delivery device has been placed in the correct position, possibly with the aid of an ultrasound or other imaging device, the method comprises the step of delivering energy from an energy source coupled to the energy delivery device. The energy is delivered through the energy delivery device to a first volume of tissue of the organ, in which the energy delivery device has been positioned. Energy is delivered until at least a portion of the first volume is vaporized or sublimated and a cavity is formed in the organ tissue. According to some embodiments, during or after energy delivery, gaseous side-products generated by tissue vaporization or sublimation can be removed, e.g. by suction, as described above. The method further includes the step of removing the energy delivery device from the organ. If needed, prior to removing or after removing, the energy delivery device can be re-positioned in a different position inside the organ, to repeat the above steps and remove by vaporization and/or sublimation a further portion of tissue.

The tissue can be hard tissue, such as bone or the like, or soft tissue, such as liver, thyroid, pancreas, brain, or other organs which may need treatment. In particular if soft tissue is treated, the volume of the cavity thus formed can be reduced, e.g. by massage on the organ.

According to some embodiments, the method can further include the step of introducing in the cavity formed by tissue vaporization or sublimation, at least one medically active element. In some embodiments, the method includes the step of introducing in the cavity thus formed at least one of the following: a medicament, a drug, a slow-absorption drug, a radioactive seed, such as a seed for brachytherapy, a chemotherapeutic agent, a combination thereof. The method allows forming a cavity in the organ to be treated without resorting to cutting instruments, which would destroy also portions of healthy tissue surrounding the area where the tumor to be treated is positioned.

While in some embodiments the tissue to be removed can be a benign or malign tumoral tissue, the method is not limited to removal of tumoral tissue. More in general, a mini-invasive surgical method is disclosed, aimed at generating a cavity in an organ in a body of a patient, for instance an organ which is difficult to reach. The method disclosed herein suggests a new way of mini-invasively reaching the site where tissue is to be removed, reducing as far as possible any impact on the surrounding tissue. This can be of paramount importance, for instance, when the need exists to preserve the integrity of surrounding tissue, such as in brain surgery.

Figure 21A:
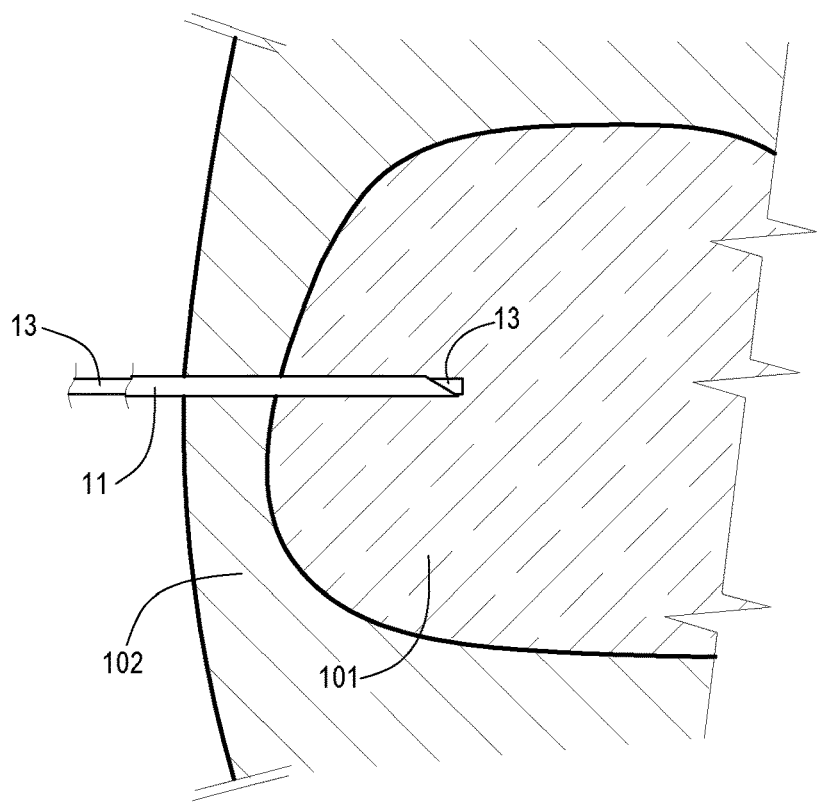
FIGS. 21A, 21B, 21C and 21D illustrate steps of a further method according to the present disclosure.
Figure 21B:
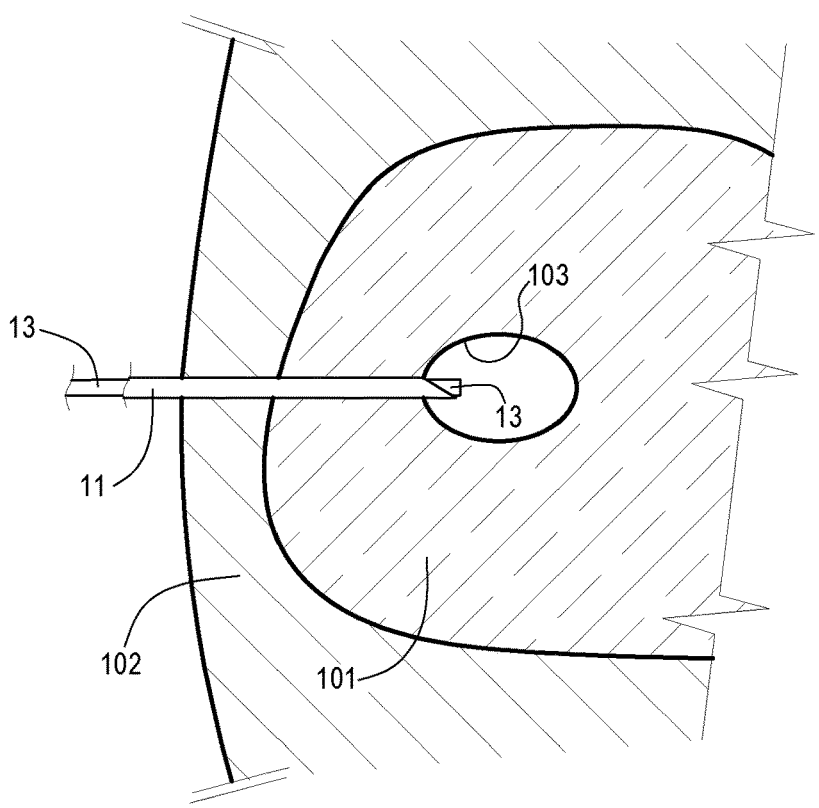

FIGS. 21A, 21B, 21C, 21D pictorially illustrate steps of a method involving tissue removal in a generic organ 101 through an introducer 11 and an energy delivery device 13. In the exemplary embodiment of FIGS. 21A-21D the introducer 11 includes a hollow needle and the energy delivery device 13 includes an optical fiber. The energy source may include a laser source. In FIG. 21A the introducer 11 and the optical fiber 13 have been introduced through surrounding tissue 102 in the organ 101 to be treated. In FIG. 21B a cavity 103 has been generated by energy-tissue interaction and tissue vaporization and/or sublimation. Resulting gaseous by-products can be removed as described above, through the introducer 11.

Figure 21C:
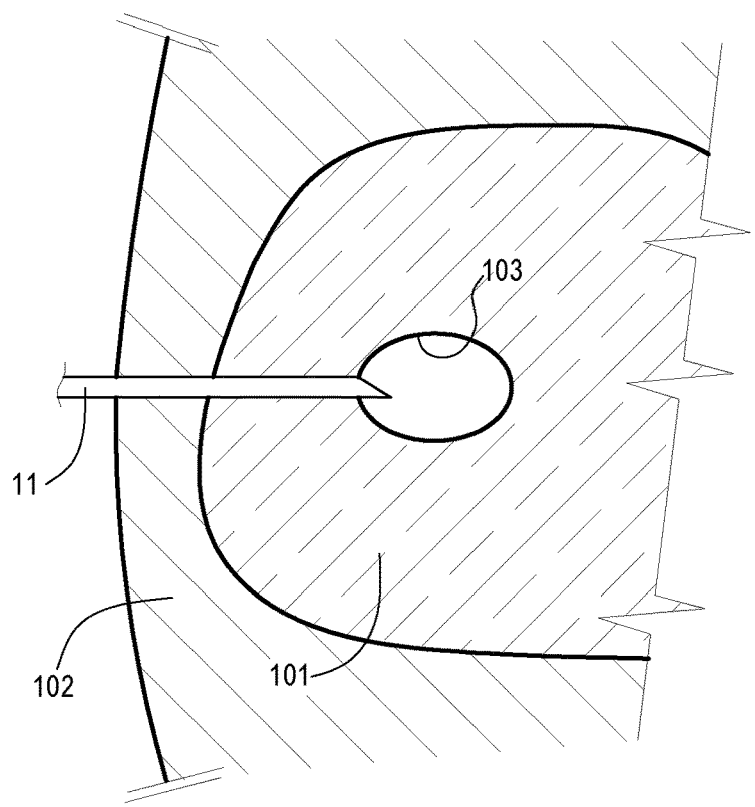
Figure 21D:
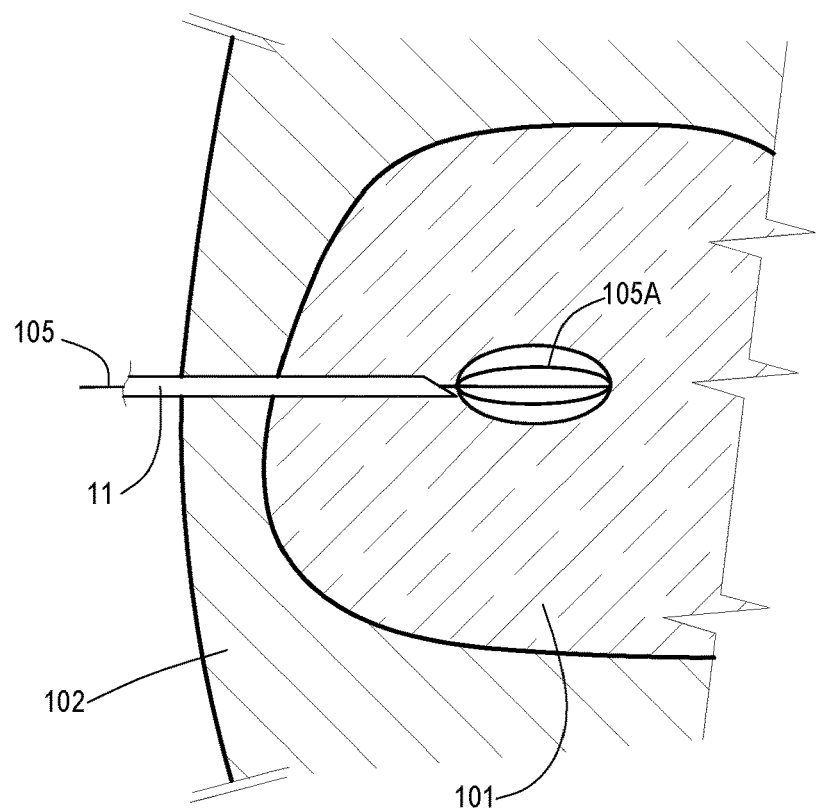

In FIG. 21C the optical fiber 13 has been removed, while the introducer 11 is still in place. The cavity 103 has been generated in the organ 101. In a further step of the method a basket, for example a shape memory basket 105, 105A can be introduced through the introducer 11 and the head 105A thereof can be expanded in the cavity 103, to prevent the cavity 103 from collapsing. FIG. 21D illustrates the expanded basket 105, 105A. Expandable baskets useful in the present method are known in the art. A basket is disclosed in US20180042625.

According to some embodiments, using a basket 105, 105, the cavity 103 can be maintained in the expanded status, for instance, in order to facilitate introduction therein of a medium, such as a liquid or semi-liquid medium, such as a drug carrier.

In some embodiments, a different medium, such as a solid medium can be introduced in the cavity. For instance, radioactive seeds for brachytherapy can be placed in the expanded cavity 103.

The basket can be recoverable. The method can thus include a step of introducing basket in the cavity generated by tissue vaporization or sublimation and a subsequent step of removing the basket from the cavity. According to other embodiments, the basket can be left in the cavity and can be made of absorbable materials.

According to some embodiments, nanoparticles, for instance gold or iron-based nanoparticles as drug carriers can be introduced in the cavity 103. Drugs, such as monoclonal drugs, for instance monoclonal antibodies can be introduced in the cavity 103, possibly attached to suitable carriers, such as nanoparticles.

Drugs or medicaments can be conveyed in a liquid or semi-liquid suspension. An expandable basket 105, 105A can prevent cavity reduction and facilitate the insertion of the suspension. In some embodiments, the basket can be retained in place until the drug has been absorbed.

In other embodiments, for instance if a semi-liquid or highly viscous carrier is used, a basket may be dispensed with or may be removed soon after inoculation of the drug suspension.

Figure 22:
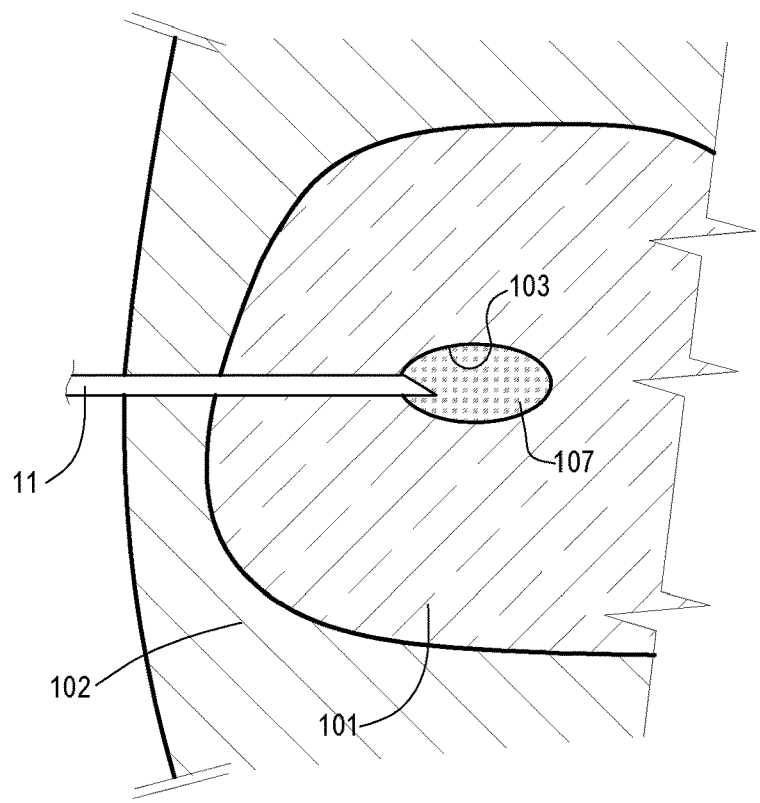
FIG. 22 illustrates a modified step of the method of FIGS. 21A-21D.

FIG. 22 illustrates a cross sectional view similar to FIGS. 21A-21D, wherein the cavity 103 has been filled with a liquid, semi-liquid or gel substance 107. The substance 107 may contain a drug or medicament, and may in turn comprise particles, such as nanoparticles used as drug carriers. The filling substance can be introduced through the introducer 11 or through a cannula inserted into the organ 101. The introducer 11 can be used also for the insertion of the basket 105, 105A. In some embodiments, the basket 105, 105A can be removed along with the introducer 11 from the organ 101 upon injection of the substance 107. The tissue wall surrounding the introducer or needle 11 can collapse after removal of the needle 11, such that reverse flow of the substance 107 through the perforation can be prevented.

Figure 23:
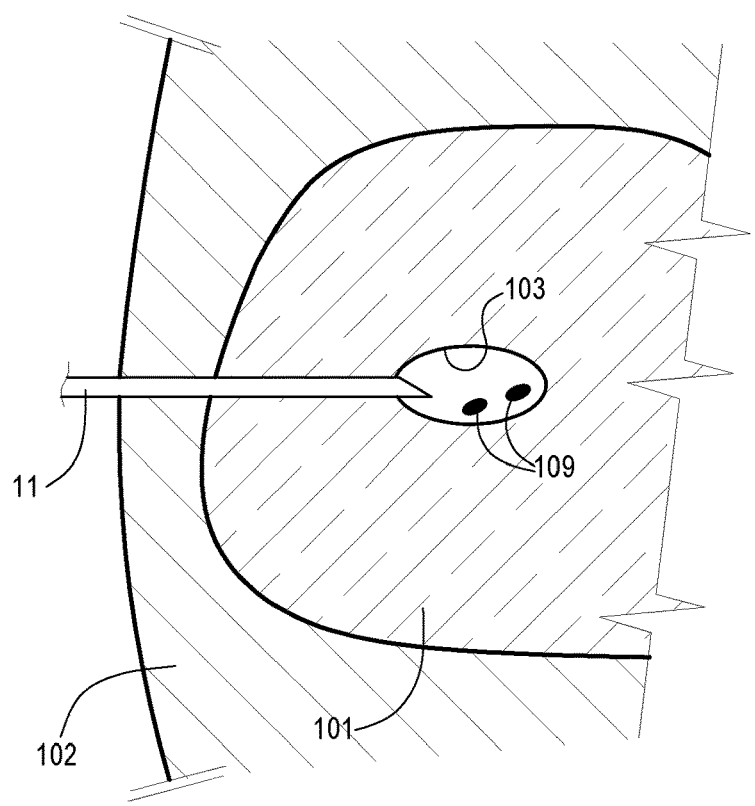
FIG. 23 illustrates a further modified step of the method of FIGS. 21A-21D.

FIG. 23 illustrates a cross sectional view similar to FIGS. 21A-21D, 22, wherein a solid substance, such as radioactive seeds 109, has been placed in the cavity 103. While in FIG. 23 no basket is shown in the cavity 103, in other embodiments, the cavity 103 may be maintained in its expanded condition by a basket 105, 105A, as described above. The use of a basket or other effectors aimed at preserving the inner volume of the cavity 103 may be beneficial when the cavity 103 has been formed in a soft tissue, or is surrounded by soft tissue. In some embodiments, the cavity 103 may be formed in harder tissue, such as bone tissue or cartilaginous tissue. An effector, such as a basket, aimed at maintaining the cavity in its expanded condition could then be dispensed with.

While the invention has been described in terms of various specific embodiments, it will be apparent to those of ordinary skill in the art that many modifications, changes, and omissions are possible without departing form the spirit and scope of the claims. In addition, unless specified otherwise herein, the order or sequence of any process or method steps may be varied or re-sequenced according to alternative embodiments.

For instance, while the above described exemplary embodiments use laser sources and laser energy to obtain tissue ablation through vaporization, the option is not ruled out of using a different power source, such as a radiofrequency power source, and respective energy delivery device, to deliver the energy in the tissue volumes where ablation is required.

What is claimed is:

1. A method of treating benign prostatic hyperplasia in a patient in need of said treatment, comprising the following steps:
    trans-perineally introducing at least one laser energy delivery fiber through a perineal area of the patient in a first position in a prostate of the patient, wherein the laser energy delivery fiber has a laser emitting fiber tip;
    delivering laser energy from a laser source through the laser emitting fiber tip to a first volume of prostrate tissue placed in front of the laser emitting fiber tip, until said first volume is vaporized or sublimated and a cavity is formed in the prostate tissue;
    pulling back the laser energy delivery fiber from the first position to a second position;
    delivering energy from the laser energy source through the laser emitting fiber tip to a second volume of prostate tissue placed in front of the laser emitting fiber tip while the laser energy delivery fiber is in the second position, until said second volume is vaporized or sublimated and the cavity is enlarged;
    removing the laser energy delivery fiber from the prostate; and
    reducing the volume of the cavity such that compression of the urethra by prostate tissue surrounding the urethra is relieved.

2. The method of claim 1, further comprising the step of removing vapor or gas resulting from the tissue vaporization or sublimation while energy is delivered through the laser energy delivery fiber.

3. The method of claim 1, wherein the laser energy delivery fiber is arranged in a hollow needle and further comprising the step of removing vapor or gas resulting from the tissue vaporization or sublimation through an annular gap between the laser energy delivery fiber and the hollow neeedle.

4. The method of claim 3, wherein the step of removing vapor or gas comprises the step of applying a negative pressure through the annular gap.

5. The method of claim 3, wherein the step of removing vapor or gas comprises the step of circulating a clean fluid medium in the cavity.

6. The method of claim 3, wherein the step of removing vapor or gas comprises the step of fluidly coupling a vacuum pump to the annular gap between the laser energy delivery do fiber and the hollow needle.

7. The method of claim 1, further comprising the steps of:
introducing an inflatable balloon in the urethra of the patient;
inflating said inflatable balloon;
deflating said inflatable balloon after sublimation or vaporization of the tissue; and
removing the inflatable balloon from the urethra.

8. The method of claim 7, further comprising the step of circulating a fluid in the balloon.

9. The method of claim 8, further comprising the step of controlling the temperature of the fluid circulating in the balloon.

10. The method of claim 7, wherein said balloon has at least one enlarged terminal end adapted to maintain the balloon in position during treatment.

11. The method of claim 1, further comprising the steps of:
introducing a trans-rectal imaging probe in the rectum of the patient; and
performing the treatment under imaging control through the trans-rectal imaging probe.

12. The method of claim 1, further comprising the steps of:
introducing at least one temperature sensing device in the prostate; and
detecting the temperature in at least one location inside the prostate during energy delivering.

13. The method of claim 12, further comprising the step of controlling the laser source based upon temperature information from the temperature sensing device.

14. The method of claim 12, wherein the step of introducing at least one temperature sensing device comprises the step of introducing said temperature sensing device between a volume of action of the laser energy delivery fiber and a critical structure of the prostate.

15. The method of claim 14, wherein the critical structure of the prostate is one of an urethra, a prostate capsule and neuro-vascular bundles around the prostate.

16. The method of claim 12, wherein the temperature sensing device is introduced trans-perineally in the prostate.

17. The method of claim 1, further comprising the step of performing a trans-rectal massage of the prostate after formation of said cavity, promoting cavity collapse.

18. A method of treating benign prostatic hyperplasia in a patient, the method comprising the steps of:
providing a laser energy delivery fiber with a laser emitting fiber tip;
introducing the laser energy delivery fiber through a perineal area of the patient to a first position in a prostrate of the patient;
transmitting laser energy from the fiber tip for a first duration, the laser energy and the first duration being configured to vaporize or sublimate a first volume of the prostrate of the patient, said transmitting of the laser energy into the first volume being in an axial direction of the laser energy delivery fiber at the fiber tip;
moving the laser energy delivery fiber from said first position to a second position in the prostrate of the patient, said second position being closer to the perennial area of the patient than said first position;
transmitting laser energy from the fiber tip for a second duration, the laser energy and the second duration being configured to vaporize or sublimate a second volume of the prostrate of the patient, said transmitting of the laser energy into the second volume being in the axial direction of the laser energy delivery fiber at the fiber tip.

19. A method in accordance with claim 18, wherein:
said moving of the laser energy delivery fiber from said first position to said second position includes moving the laser energy delivery fiber in a withdrawal from the prostrate direction.

20. A method in accordance with claim 18, wherein:
said first volume is downstream of the laser energy in the axial direction of the fiber at the fiber tip in the first position;
said second volume is downstream of the laser energy in the axial direction of the fiber at the fiber tip in the second position.

21. A method in accordance with claim 18, further comprising:
determining a removal portion of the prostrate of the patient which is to be removed;
configuring the first position to arranged the first volume at part of the removal portion furthest from the perineal area.

* * * * *